(12) United States Patent
Rezach et al.

(10) Patent No.: US 12,133,665 B2
(45) Date of Patent: Nov. 5, 2024

(54) SURGICAL INSTRUMENT AND METHOD

(71) Applicant: WARSAW ORTHOPEDIC INC., Warsaw, IN (US)

(72) Inventors: William Alan Rezach, Covington, TN (US); Charles G. Fisher, Vancouver (CA); Marcel F. Dvorak, Vancouver (CA); Lawrence G. Lenke, New York, NY (US); Ronald A. Lehman, Tenafly, NJ (US)

(73) Assignee: WARSAW ORTHOPEDIC INC., Warsaw, IN (US)

( * ) Notice: Subject to any disclaimer, the term of this patent is extended or adjusted under 35 U.S.C. 154(b) by 181 days.

(21) Appl. No.: 17/846,216

(22) Filed: Jun. 22, 2022

(65) Prior Publication Data

US 2022/0323121 A1    Oct. 13, 2022

Related U.S. Application Data

(63) Continuation of application No. 17/078,631, filed on Oct. 23, 2020, now Pat. No. 11,426,215.

(51) Int. Cl.
*A61B 17/70*    (2006.01)
*A61B 17/00*    (2006.01)

(52) U.S. Cl.
CPC ...... *A61B 17/7082* (2013.01); *A61B 17/7091* (2013.01); *A61B 2017/00367* (2013.01)

(58) Field of Classification Search
CPC ............ A61B 17/7082; A61B 17/7085; A61B 17/7091; A61B 2017/00367
USPC ........................................................ 606/86 A
See application file for complete search history.

(56) References Cited

U.S. PATENT DOCUMENTS

2014/0114363 A1*  4/2014  Stevenson .......... A61B 17/7082
                                                        606/305
2014/0180298 A1*  6/2014  Stevenson .......... A61B 17/7082
                                                        606/104

* cited by examiner

*Primary Examiner* — Eduardo C Robert
*Assistant Examiner* — Christina Negrellirodriguez
(74) *Attorney, Agent, or Firm* — Sheridan Ross P.C.

(57) ABSTRACT

A surgical instrument comprises a member being engageable to a spinal implant configured for connection to a bone fastener shaft. An actuator is connected to the member. A latch is connected to the actuator and the connection is configured to change between at least one non-locked orientation such that the actuator is movable relative to the member and a locked orientation such that the actuator is fixed relative to the member. Systems, spinal constructs, implants and methods are disclosed.

20 Claims, 21 Drawing Sheets

SURGICAL INSTRUMENT AND METHOD

CROSS-REFERENCE TO RELATED APPLICATIONS

This application is a continuation of U.S. patent application Ser. No. 17/078,631, filed on Oct. 23, 2020. This application is expressly incorporated herein by reference, in its entirety.

TECHNICAL FIELD

The present disclosure generally relates to medical devices for the treatment of musculoskeletal disorders, and more particularly to a surgical system and method for treating a spine.

BACKGROUND

Spinal disorders such as degenerative disc disease, disc herniation, osteoporosis, spondylolisthesis, stenosis, scoliosis, kyphosis and other curvature abnormalities, tumor, and fracture may result from factors including trauma, disease and degenerative conditions caused by injury and aging. Spinal disorders typically result in symptoms including pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. As part of these surgical treatments, spinal constructs, which include implants such as bone fasteners, connectors, plates and vertebral rods are often used to provide stability to a treated region. These implants can redirect stresses away from a damaged or defective region while healing takes place to restore proper alignment and generally support the vertebral members. Surgical instruments are employed, for example, to engage the fasteners for attachment to the exterior of two or more vertebral members. This disclosure describes an improvement over these prior technologies.

SUMMARY

In one embodiment, a surgical instrument is provided. The surgical instrument includes a member being engageable to a spinal implant configured for connection to a bone fastener shaft. An actuator is connected to the member. A latch is connected to the actuator and the connection is configured to change between at least one non-locked orientation such that the actuator is movable relative to the member and a locked orientation such that the actuator is fixed relative to the member. In some embodiments, systems, spinal constructs, implants and methods are disclosed.

In one embodiment, the surgical instrument includes a member being engageable to a spinal implant configured for connection to a bone fastener shaft. A handle is connected to the member and includes a pivot. A latch is connected to the pivot and is engageable to the member. The engagement is configured to change between an open position such that the handle is movable relative to the member, an intermediate position such that the handle is fixed relative to the member and a closed position such that the handle is movable relative to the member.

In one embodiment, a surgical system is provided. The surgical system includes a bone fastener shaft configured for fixation to vertebral tissue. A spinal implant receiver is configured for connection to the bone fastener shaft. A surgical instrument includes an actuator and a member engageable to the spinal implant receiver. The surgical instrument further includes a latch connected to the actuator and the connection is configured to change between at least one non-locked orientation such that the actuator is movable relative to the member and a locked orientation such that the actuator is fixed relative to the member.

BRIEF DESCRIPTION OF THE DRAWINGS

The present disclosure will become more readily apparent from the specific description accompanied by the following drawings, in which.

DETAILED DESCRIPTION

Figure 1:
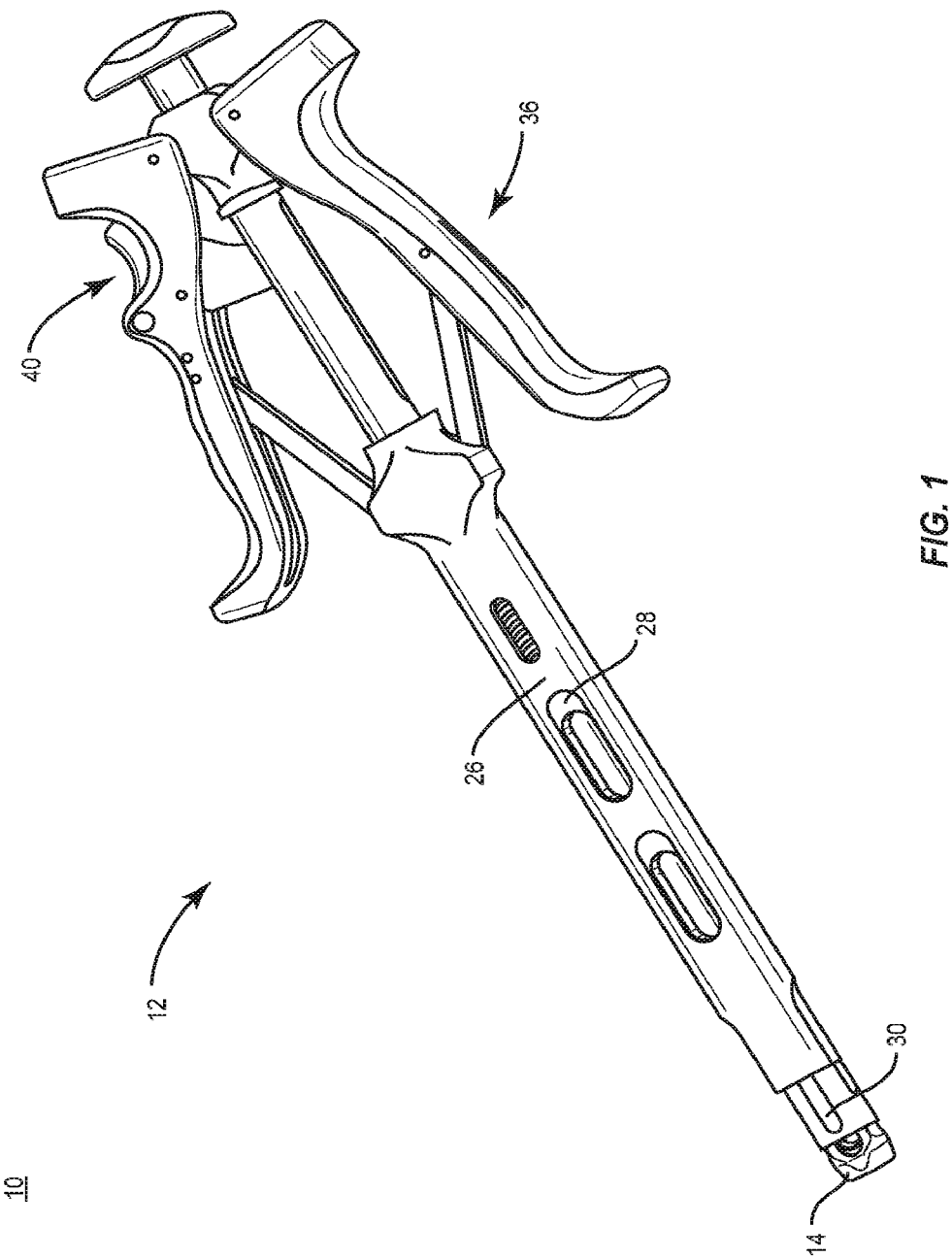
FIG. 1 is a perspective view of components of one embodiment of a surgical system in accordance with the principles of the present disclosure.

The exemplary embodiments of a surgical system are discussed in terms of medical devices for the treatment of musculoskeletal disorders and more particularly, in terms of a surgical system and a method for treating a spine. In some embodiments, the present surgical system includes a surgical instrument, for example, an inserter engageable to a spinal implant, for example, a receiver. In some embodiments, the present surgical system includes an inserter including an actuator, for example, a handle and a latch disposable in one or more orientations, for example, locked and non-locked orientations such that a spinal implant, for example, a receiver can be connected to and disconnected from the inserter.

In some embodiments, the present surgical system includes a surgical instrument, for example, an inserter configured to connect a spinal implant to a bone fastener shaft. In some embodiments, the inserter includes a member, an actuator and a latch, for example, a trigger mechanism. In some embodiments, the trigger mechanism includes a biasing member, for example, a torsion spring. In some embodiments, the trigger mechanism is configured to engage the actuator in a non-locked orientation and a locked orientation. In some embodiments, in the non-locked orientation, the actuator is movable relative to the member. In some embodiments, in the locked orientation, the actuator is fixed relative to the member. In some embodiments, the actuator includes a pair of handles. In some embodiments, the handles are movable to position the inserter into multiple orientations. In some embodiments, the inserter is configured as a locking tool such that a spinal implant, for example, a receiver, can be connected to or disconnected from an end, for example, a distal end of the inserter.

In some embodiments, the present surgical system includes a surgical inserter configured for connection to a spinal implant receiver. In some embodiments, the inserter includes a proximal end and a distal end. In some embodiments, the inserter includes a member. In some embodiments, the member includes an outer sleeve, an intermediate sleeve and an inner shaft. In some embodiments, the inserter includes a latch, for example, a locking mechanism including a finger engagement surface. In some embodiments, the inserter includes an actuator, for example, a pair of handles. In some embodiments, the latch is connected to the actuator in at least one non-locked orientation such that the actuator is movable relative to the member and a locked orientation such that the actuator is fixed relative to the member. In some embodiments, the actuator is movable between an open position including the non-locked orientation, an intermediate position including the locked orientation and a closed position including the non-locked orientation.

In some embodiments, the actuator is oriented in the open position. In some embodiments, in the open position, the receiver is loaded into the distal end. In some embodiments, in the open position, the receiver can be loaded and/or removed from the distal end of the inserter. In some embodiments, in the open position, spring tabs of the intermediate sleeve are disposed in a flexed outward state and the springs tabs do not engage rocker holes of the receiver.

In some embodiments, the actuator is oriented in the intermediate position. In some embodiments, in the intermediate position, the actuator is locked until the latch is manually depressed by a user. In some embodiments, the latch locks with a pin that is centrally disposed on a shaft of the member to prevent the actuator from opening or closing. In some embodiments, in the intermediate position, the receiver is secured to the distal end. In some embodiments, in the intermediate position, the outer sleeve translates in a direction, for example, axially. In some embodiments, the outer sleeve translates a distance, for example, 2.5 to 3.0 mm. In some embodiments, the intermediate sleeve does not translate when the outer sleeve translates. In some embodiments, the actuator is released to disconnect the receiver from the distal end. In some embodiments, the spring tabs are compressed by the outer sleeve to engage the receiver rocker holes as the actuator is positioned from the open position to the intermediate position.

In some embodiments, the actuator is oriented in the closed position. In some embodiments, the latch is depressed and the actuator is compressed to position the inserter in the locking orientation to lock the receiver to the distal end. In some embodiments, in the closed position, the actuator is released when the actuator is compressed. In some embodiments, in the closed position, the outer sleeve translates axially. In some embodiments, the outer sleeve translates a distance of 5.0 to 6.0 mm. In some embodiments, the intermediate sleeve does not translate when the outer sleeve translates. In some embodiments, the tip of the inner shaft translates while the receiver is connected to the distal end via the spring tabs and the outer sleeve continues to translate over the spring tabs as the actuator is positioned from the intermediate position to the closed position. In some embodiments, in the closed position, the inner shaft pushes an implant crown in a downward direction and into the receiver.

In some embodiments, the actuator is oriented in the open position. In some embodiments, in the open position, the receiver is loaded into the distal end. In some embodiments, in the open position, the receiver can be loaded and/or removed from the distal end of the inserter. In some embodiments, in the open position, spring tabs of the outer sleeve are in a flexed inward state such that the spring tabs can be inserted into the interior features of the receiver.

In some embodiments, the actuator is oriented in the intermediate position. In some embodiments, in the intermediate position, the actuator is locked until the latch is manually depressed by a user. In some embodiments, the latch locks onto a pin that is centrally disposed on a shaft of the member to prevent the actuator from opening or closing. In some embodiments, in the intermediate position, the receiver is connected to the distal end. In some embodiments, in the intermediate position, the outer sleeve remains fixed and the inner shaft translates in a direction, for example, axially. In some embodiments, the inner shaft translates a distance of, for example 2.0 to 3.0 mm. In some embodiments, the actuator is released to disconnect the receiver from the distal end. In some embodiments, in the intermediate position, the spring tabs are forced in an outward orientation by translation of the inner shaft to engage the interior features of the receiver.

In some embodiments, the actuator is oriented in the closed position. In some embodiments, the latch is depressed and the actuator is compressed to position the inserter in the locking orientation to lock the receiver to the distal end. In some embodiments, once the actuator has been compressed and the inserter is in the locking orientation, the actuator is released in order to return the inserter into the open position. In some embodiments, in the closed position, the outer sleeve remains fixed and the inner shaft translates in a direction, for example, axially. In some embodiments, the inner shaft translates a distance of 5.0 to 6.0 mm. In some embodiments, in the closed position, the receiver is connected to the distal end via the spring tabs as the inner shaft translates axially beyond the spring tabs. In some embodiments, a tip of the inner shaft pushes an implant crown in a downward direction and into the receiver.

In some embodiments, the present system includes a surgical instrument including an inserter. In some embodiments, the inserter includes a member, a latch and an actuator. In some embodiments, the latch is connected to the actuator in at least one non-locked orientation such that the actuator is movable relative to the member in open and closed positions and a locked orientation such that the actuator is fixed relative to the member and the actuator is in an intermediate position.

In some embodiments, the latch includes a biasing member, for example, a torsion spring and a selected ramp geometry including a plurality of ramp surfaces that facilitate movement of the actuator relative to the inserter. In some embodiments, the ramp surfaces enable the actuator to fully return to an open position from a closed position without the actuator becoming disposed in an intermediate position. For example, upon manipulation of the actuator, the ramp surfaces allow the actuator to automatically return to an open position from the closed position. In some embodiments, the plurality of ramp surfaces include a first ramp and a second ramp disposed at a selected angular orientation relative to the first ramp. In some embodiments, the torsion spring and the ramps enable the latch to be oriented in the non-locked and locked orientations. In some embodiments, the first ramp is disposed at a selected incline relative to the second ramp. In some embodiments, the ramps are configured for engagement with a locking pin disposed on a shaft of the inserter such that the member is slidably engageable with the ramps to place the latch into the non-locked and locked orientations. In some embodiments, a compression spring facilitates return of the actuator to the open position.

In some embodiments, when the actuator is disposed in an open position, the locking pin contacts the first ramp or an end surface of the latch and the latch is oriented in the non-locked orientation. In some embodiments, when the actuator is disposed in an intermediate position, the actuator is compressed and the locking pin translates into a slot defined from a surface of the latch and engages with the slot to place the latch into the locked orientation. In some embodiments, the latch is depressed and the locking pin engages with the second ramp. In some embodiments, when the actuator is disposed in the closed position, the actuator is compressed and the locking pin translates along the second ramp surface. In some embodiments, when the actuator is released, the locking pin translates from the second ramp to the first ramp such that the latch is oriented into the non-locked orientation.

In some embodiments, the ramps of the latch enable the inserter to automatically return to an open position and prevents the inserter from capture in the intermediate position. In some embodiments, when the actuator is compressed, the inserter is automatically returned to an open position from the closed position. In some embodiments, when the inserter is automatically returned via compression of the actuator, the latch bypasses the slot such that the inserter returns to the open position. In some embodiments, the automatic return of the inserter into the open position prevents a user, for example, a surgeon from having to depress the latch to release the implant from the inserter.

In some embodiments, the present surgical system includes a surgical inserter employed with a method for connecting a spinal implant receiver to a bone fastener shaft. In some embodiments, the method includes the step of introducing an inserter. In some embodiments, the inserter includes a proximal end and a distal end. In some embodiments, the inserter includes a member, a latch and an actuator. In some embodiments, the method includes the step of disposing the inserter in an initial open position to load an implant, for example, a receiver to the distal end. In some embodiments, in the open position, the receiver is loaded into the distal end. In some embodiments, the method includes the step of disposing the inserter in an intermediate position to connect the receiver to the distal end. In some embodiments, in the intermediate position, the actuator is locked until the latch is manually depressed by a user. In some embodiments, the method includes the step of disposing the inserter into a closed position to lock the receiver to the distal end. In some embodiments, in the closed position, the actuator is released when the actuator is compressed.

In some embodiments, the system of the present disclosure may be employed to treat spinal disorders, for example, degenerative disc disease, disc herniation, osteoporosis, spondylolisthesis, stenosis, scoliosis and other curvature abnormalities, kyphosis, tumor and fractures. In some embodiments, the system of the present disclosure may be employed with other osteal and bone related applications, including those associated with diagnostics and therapeutics. In some embodiments, the disclosed system may be alternatively employed in a surgical treatment with a patient in a prone or supine position, and/or employ various surgical approaches to the spine, including anterior, posterior, posterior mid-line, direct lateral, postero-lateral, and/or antero-lateral approaches, and in other body regions. The system of the present disclosure may also be alternatively employed with procedures for treating the lumbar, cervical, thoracic, sacral and pelvic regions of a spinal column. The system of the present disclosure may also be used on animals, bone models and other non-living substrates, for example, in training, testing and demonstration.

The system of the present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a surgical system including a surgical instrument, related components and methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1-15, there are illustrated components of a surgical system 10.

The components of surgical system 10 can be fabricated from biologically acceptable materials suitable for medical applications, including metals, synthetic polymers, ceramics and bone material and/or their composites. For example, the components of surgical system 10, individually or collectively, can be fabricated from materials such as stainless steel alloys, aluminum, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, for example, composites of metals and calcium-based ceramics, composites of PEEK and calcium based ceramics, composites of PEEK with resorbable polymers, totally resorbable materials, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

The components of surgical system 10, individually or collectively, may also be fabricated from a heterogeneous material such as a combination of two or more of the above-described materials. The components of surgical system 10 may be monolithically formed, integrally connected or include fastening elements and/or instruments, as described herein.

Surgical system 10 can be employed, for example, with a minimally invasive procedure, including percutaneous techniques, mini-open and open surgical techniques to deliver and introduce instrumentation and/or components of spinal constructs at a surgical site within a body of a patient, for example, a section of a spine. In some embodiments, one or more of the components of surgical system 10 are configured for engagement with existing spinal constructs, which may include spinal implants such as one or more rods, fasteners, plates and connectors. In some embodiments, the spinal constructs can be attached with vertebrae in a revision surgery to manipulate tissue and/or correct a spinal disorder, as described herein.

Figure 14:
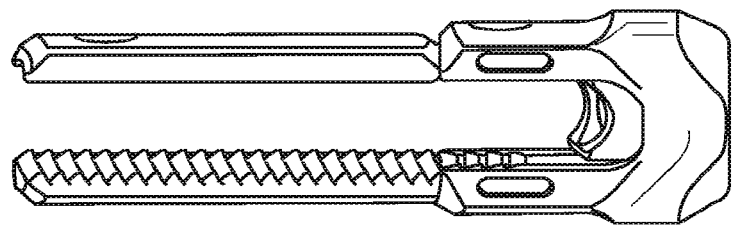
FIG. 14 is a perspective view of components of one embodiment of a surgical system in accordance with the principles of the present disclosure.
Figure 13:
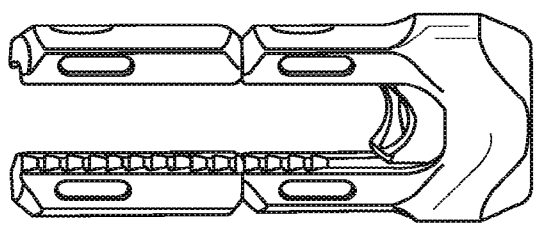
FIG. 13 is a perspective view of components of one embodiment of a surgical system in accordance with the principles of the present disclosure.
Figure 15:
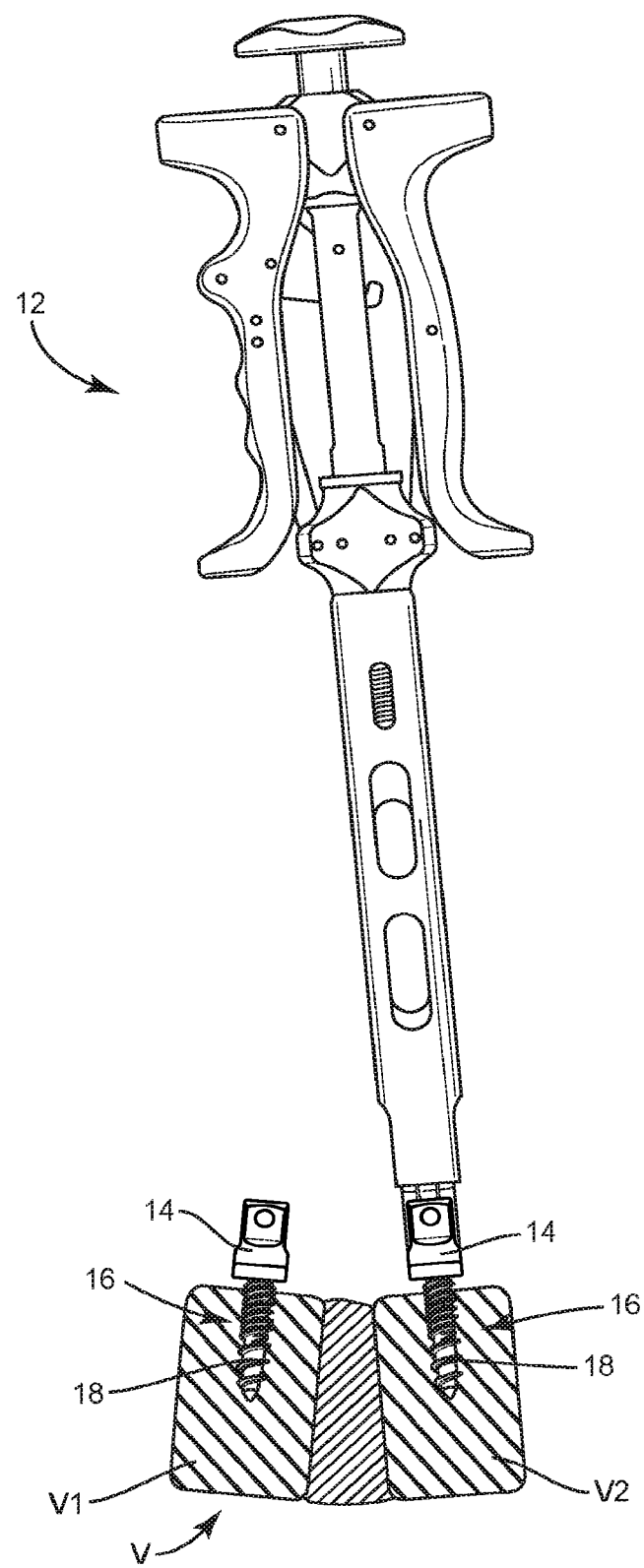
FIG. 15 is a side view of components of one embodiment of a surgical system in accordance with the principles of the present disclosure disposed with vertebrae shown in cross section.
Figure 16:
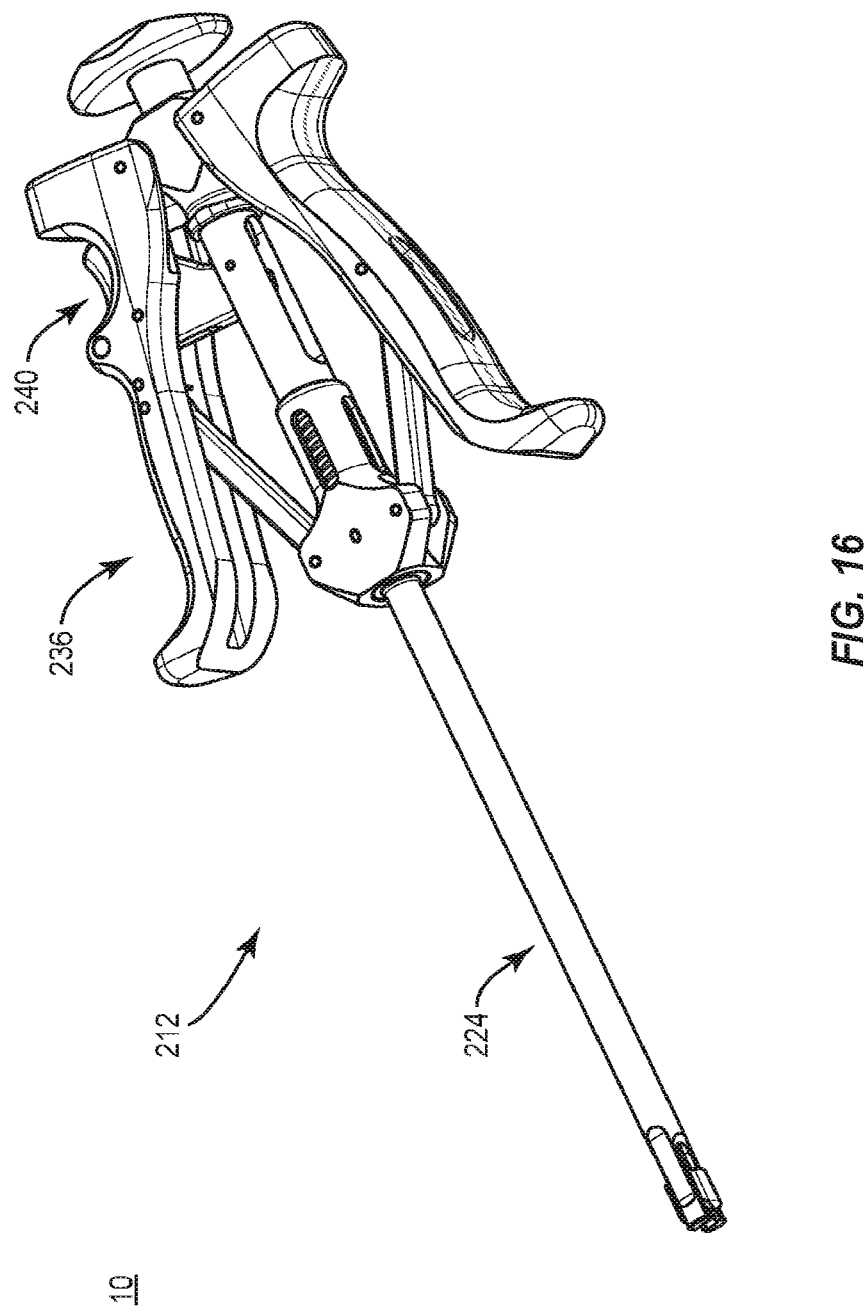
FIG. 16 is a perspective view of components of one embodiment of a surgical system in accordance with the principles of the present disclosure.

Surgical system 10 includes a surgical instrument, for example inserter 12. Inserter 12 is configured to engage a spinal implant, for example, a receiver 14 of a bone fastener 16, as shown in FIG. 13-15. Inserter 12 is configured to connect receiver 14 to a shaft 18 of bone fastener 16 that has been implanted into a surgical site, for example, vertebral tissue, as shown in FIG. 15 and described herein.

Figure 2:
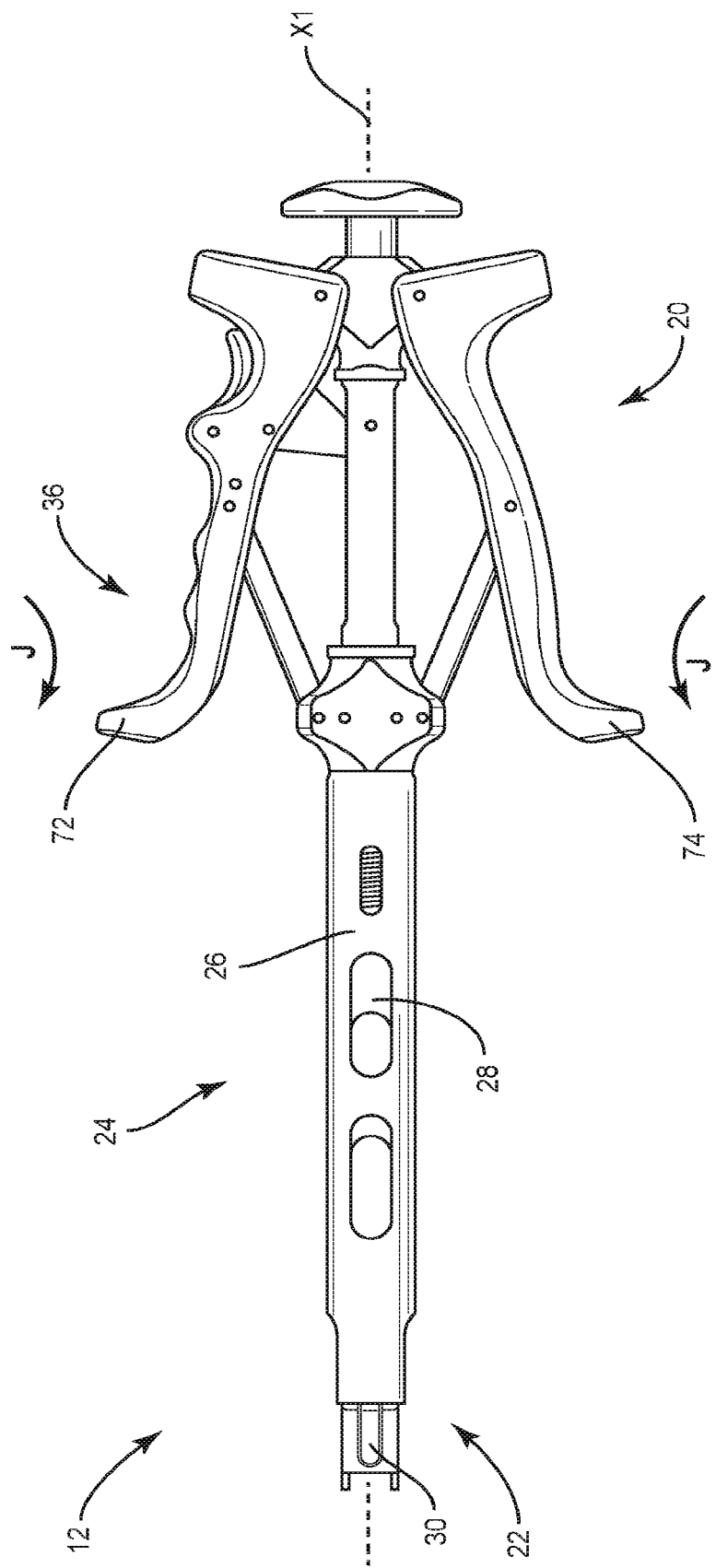
FIG. 2 is a side view of the components shown in FIG. 1.

Inserter 12 includes a proximal end 20 and a distal end 22, as shown in FIG. 2. Inserter 12 extends along and defines a longitudinal axis X1, as shown in FIG. 2. In some embodiments, inserter 12 may have various cross-section configurations, for example, oval, oblong, triangular, rectangular, square, polygonal, irregular, uniform, non-uniform, variable, tubular and/or tapered.

Figure 4:
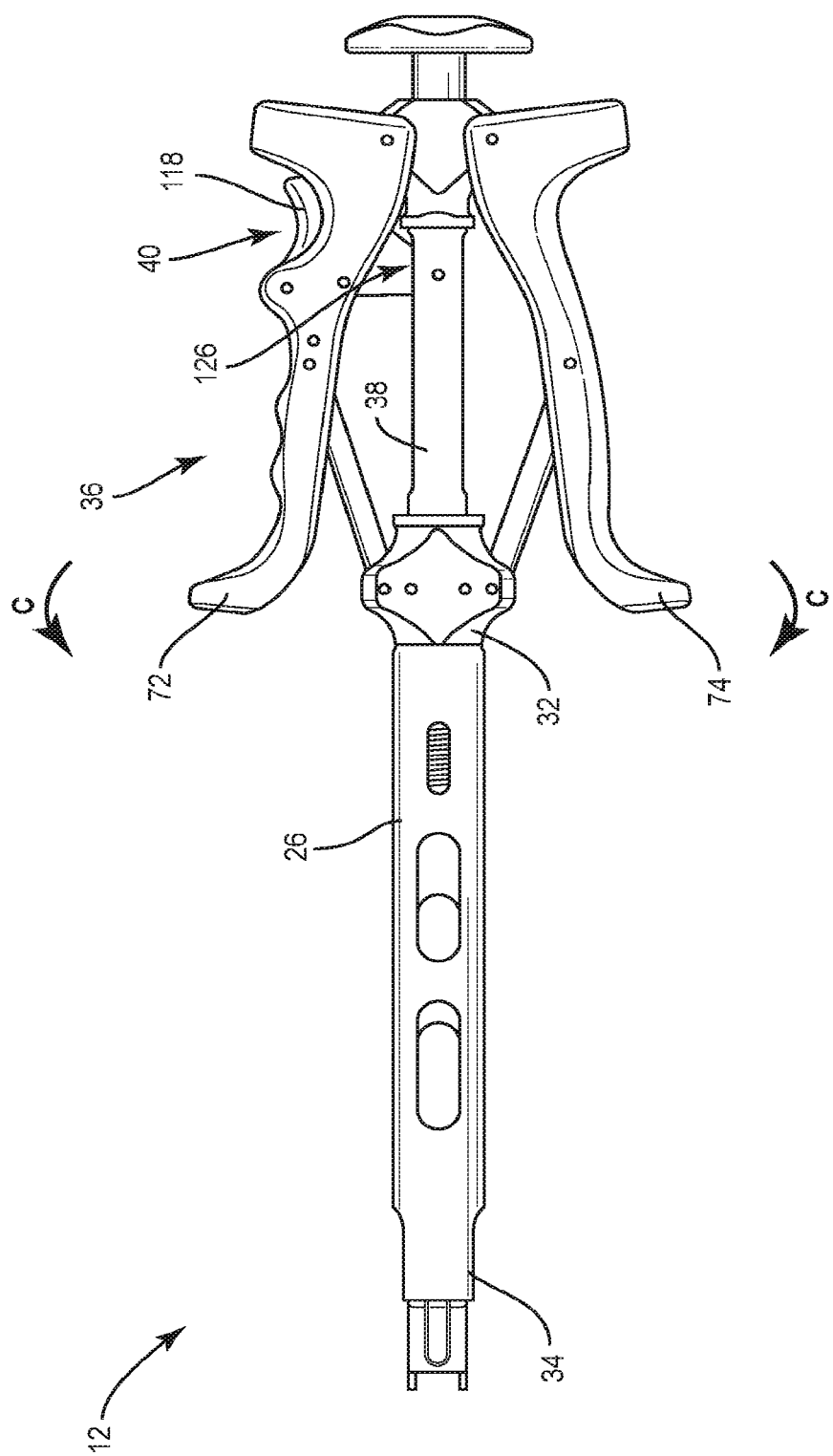
FIG. 4 is a side view of the components shown in FIG. 1.

Inserter 12 has a member 24 including an outer sleeve 26, an intermediate sleeve 28 and an inner distal tip 30, as shown in FIG. 2. Sleeve 26, sleeve 28 and tip 30 are configured to engage receiver 14. Sleeve 26 includes an end 32 and an end 34, as shown in FIG. 4. In some embodiments, sleeve 26 may have various cross-section configurations, for example, oval, oblong, triangular, rectangular, square, polygonal, irregular, uniform, non-uniform, variable, tubular and/or tapered.

End 32 is configured to engage an actuator 36, as shown in FIG. 1. Actuator 36 is movable relative to member 24, as described herein. An outer shaft 38 is disposed at end 32 and is configured for engagement to actuator 36 and a latch 40, as shown in FIG. 4 and described herein. In some embodiments, shaft 38 may have various cross-section configurations, for example, oval, oblong, triangular, rectangular, square, polygonal, irregular, uniform, non-uniform, variable, tubular and/or tapered.

Figure 3:
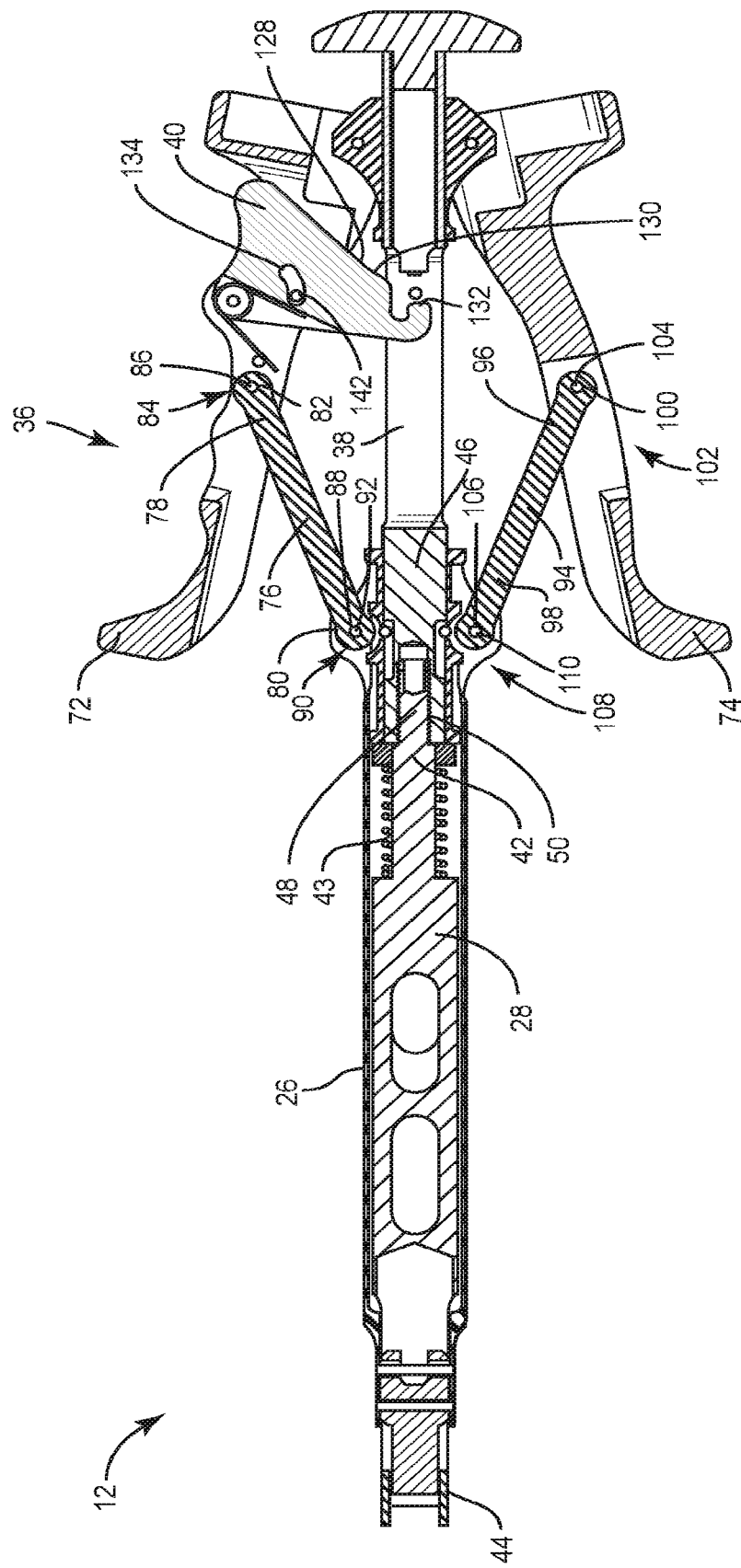
FIG. 3 is a side cross section view of the components shown in FIG. 2.
Figure 10:
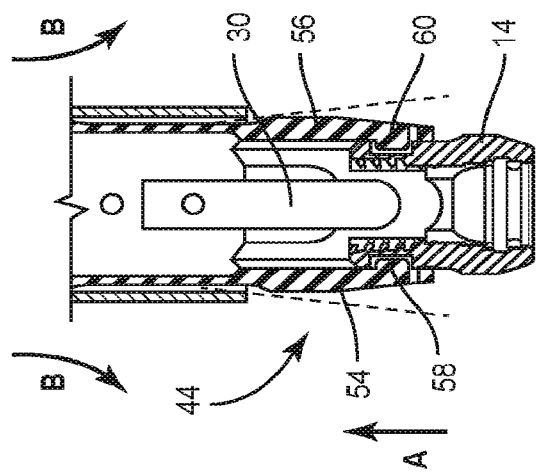
FIG. 10 is a side cross section view of components of one embodiment of a surgical system in accordance with the principles of the present disclosure.

Sleeve 28 includes an end 42 and an end 44, as shown in FIGS. 3 and 10. Sleeve 28 is in co-axial alignment relative to sleeve 26 and extends along longitudinal axis X1, as shown in FIGS. 2 and 3. Sleeve 28 is fixed relative to shaft 38. As actuator 36 is moved, sleeve 26 translates axially along sleeve 28. In some embodiments, sleeve 28 may have various cross-section configurations, for example, oval, oblong, triangular, rectangular, square, polygonal, irregular, uniform, non-uniform, variable, tubular and/or tapered.

End 42 is configured to engage an end 46 of shaft 38, as shown in FIG. 3. End 42 includes a threaded portion 48 that is configured for disposal into a threaded recess 50 of end 46, as shown in FIG. 3. Sleeve 26 is movable relative to end 38, as shown in FIGS. 3, 5, 7 and 9. A biasing member, for example, a spring 43 is configured for disposal about end 42 and is configured to provide energy in an axial direction to facilitate return movement of sleeve 26 when actuator 36 is released, as described herein.

Figure 12:
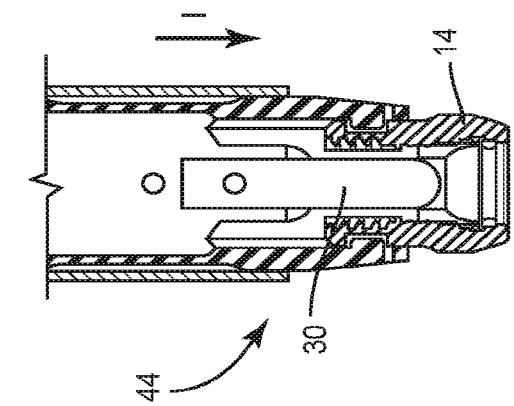
FIG. 12 is a side cross section view of the components shown in FIG. 10.
Figure 11:
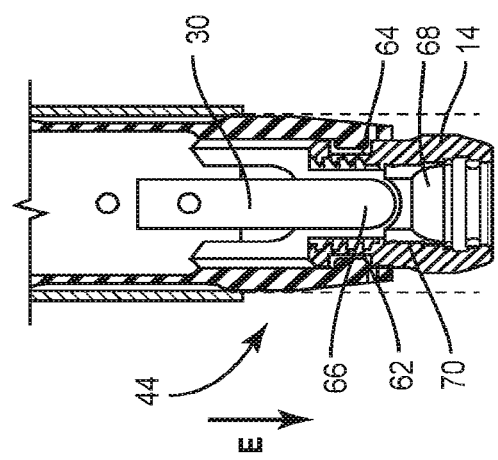
FIG. 11 is a side cross section view of the components shown in FIG. 10.

End 44 is configured to engage receiver 14, as shown in FIGS. 10-12. End 44 includes a tab 54 and a tab 56. Tabs 54 and 56 are flexible and are configured to engage end 34 of sleeve 26 and receiver 14. Tab 54 includes an inner surface that defines a projection 58 and tab 56 includes an inner surface that defines a projection 60, as shown in FIG. 10. Projections 58, 60 are configured to engage openings 62, 64 defined from a surface of receiver 14, as shown in FIG. 11.

Tip 30 is fixed to a surface of sleeve 26 and is translatable relative to sleeve 28. An end 66 of tip 30 is configured to engage a crown 68 disposed within a cavity 70 of receiver 14, as shown in FIG. 10. Crown 68 is configured for locking receiver 14 to shaft 18, as described herein. In some embodiments, tip 30 may have various cross-section configurations, for example, oval, oblong, triangular, rectangular, square, polygonal, irregular, uniform, non-uniform, variable, tubular and/or tapered.

End 20 of inserter 12 includes actuator 36, as shown in FIG. 2. Actuator 36 is movable between an open position including a non-locked orientation (FIGS. 2 and 3), an intermediate position including a locked orientation (FIGS. 4 and 5) and a closed position including a non-locked orientation (FIGS. 8 and 9), as described herein. Actuator 36 is rotatable relative to sleeve 26 such that sleeve 26 translates relative to sleeve 28 to engage receiver 14. In a natural state, actuator 36 is biased to the open position and is automatically movable from the closed position to the open position.

Actuator 36 includes a pair of lever handles 72, 74, as shown in FIG. 2 that are rotatable relative to member 24. In some embodiments, handles 72, 74 may have various cross-section configurations, for example, oval, oblong, triangular, rectangular, square, polygonal, irregular, uniform, non-uniform, variable, tubular and/or tapered. In some embodiments, an outer surface of handles 72, 74 has one or more of various surface configurations, for example, rough, threaded, arcuate, undulating, porous, semi-porous, dimpled, polished and/or textured. In some embodiments, actuator 36 includes one or more handles.

Figure 5:
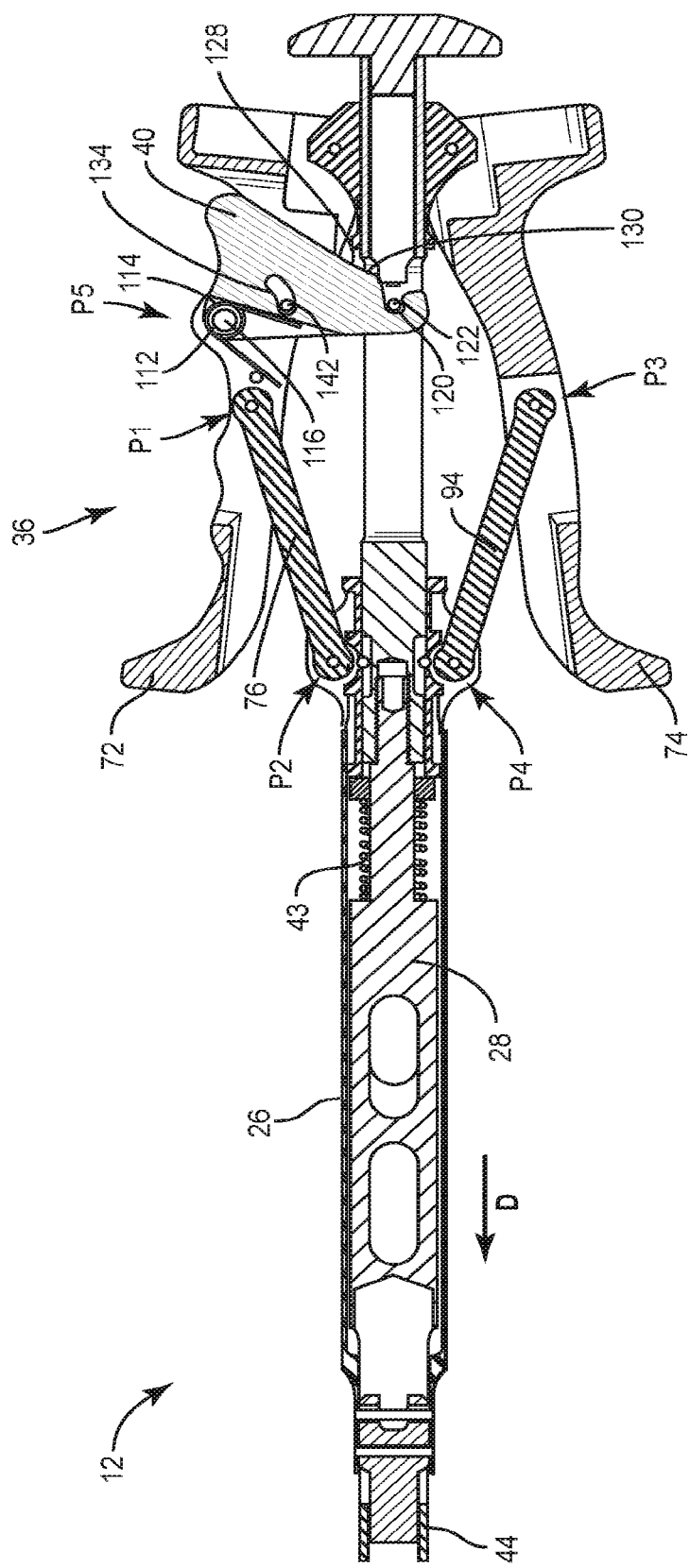
FIG. 5 is a side cross section view of the components shown in FIG. 4.

Handle 72 includes a bar linkage 76 that is rotatably engaged to member 24, as shown in FIG. 3. Linkage 76 includes an end 78 and an end 80. End 78 includes a surface that defines an opening 82. A surface of handle 72 defines an opening 84. End 78 engages handle 72 via a pin 86 that is disposed within openings 82 and 84. End 80 includes a surface that defines an opening 88. A surface of sleeve 26 defines an opening 90. End 80 engages to sleeve 26 via a pin 92 that is disposed within openings 88 and 90. Engagement between end 78 of linkage 76 and handle 72 creates a pivot point P1, as shown in FIG. 5. Engagement between end 80 of linkage 76 and sleeve 26 creates a pivot point P2, as shown in FIG. 5.

Handle 74 includes a bar linkage 94 rotatably engaged to member 24, as shown in FIG. 3. Linkage 94 includes an end 96 and an end 98. End 96 includes a surface that defines an opening 100. A surface of handle 74 defines an opening 102. End 96 engages handle 74 via a pin 104 that is disposed within openings 100 and 102. End 98 includes a surface that defines an opening 106. A surface of sleeve 26 defines an opening 108. End 98 engages to sleeve 26 via a pin 110 that is disposed within openings 106 and 108. Engagement between end 96 of linkage 94 and handle 74 creates a pivot point P3, as shown in FIG. 5. Engagement between end 98 of linkage 94 and sleeve 26 creates a pivot point P4, as shown in FIG. 5.

Figure 7:
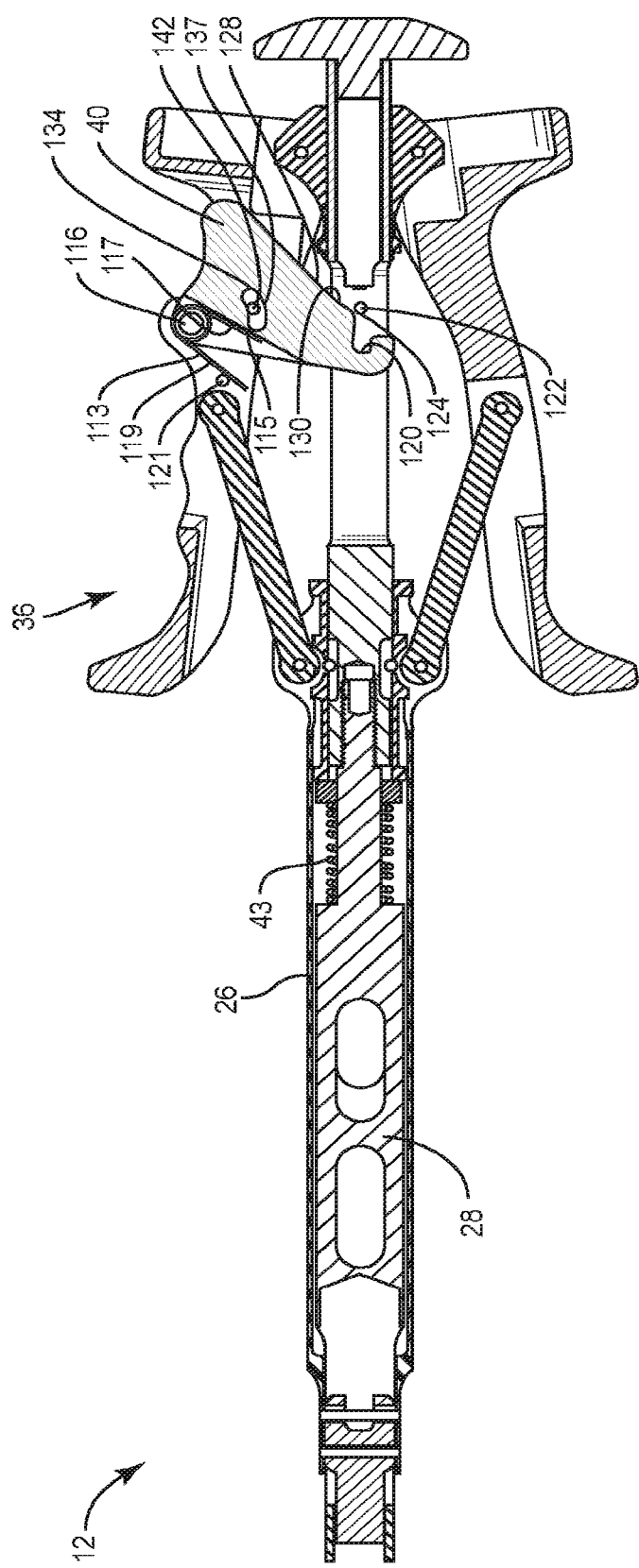
FIG. 7 is a side cross section view of the components shown in FIG. 6.

Latch 40 is connected to actuator 36 in a non-locked orientation (FIGS. 2-3 and 8-9) such that actuator 36 is movable relative to member 24 in the open position and the closed position, and a locked orientation (FIGS. 4 and 5) such that actuator 36 is fixed relative to member 24 in the intermediate position. Latch 40 is connected to actuator 36 via handle 72, as shown in FIG. 4. A surface of handle 72 defines an opening 112 and a surface of latch 40 defines an opening 114. A pin 116 is configured for disposal within openings 112 and 114 to rotatably engage latch 40 with handle 72, as shown in FIG. 5. Engagement between handle 72 and latch 40 creates a pivot point P5, as shown in FIG. 5. A biasing member, for example, a torsion spring 113 is configured for disposal with pin 116 and engagement to latch 40, as shown in FIG. 7. Spring 113 is configured to provide torque to latch 40 when pivoted into a non-locked and/or a locked orientation. An end 115 of spring 113 is configured to engage an indent 117 of latch 40 and an end 119 of spring 113 is configured for engagement with a pin 121, as shown in FIG. 7.

Latch 40 includes an outer surface that defines a trigger 118 including a finger engagement surface, as shown in FIG. 4. Trigger 118 is configured for engagement with a user such that latch 40 can be manually depressed to rotatably translate latch 40 into a selected orientation, as described herein. In some embodiments, the finger engagement surface can have one or more various surface configurations, for example, rough, threaded, arcuate, undulating, porous, semi-porous, dimpled, polished and/or textured.

Latch 40 includes a surface that defines a slot 120 configured to engage member 24 via a pin 122 disposed in a cavity 124 of shaft 38. Latch 40 is rotatable relative to actuator 36 for capture of member 24 in the intermediate position such that pin 122 is disposed in slot 120 in a locked orientation, as shown in FIG. 5 and described herein. In some embodiments, slot 120 includes a C-groove configuration. In some embodiments, slot 120 may have various cross-section configurations, for example, oval, oblong, triangular, rectangular, square, polygonal, irregular, uniform, non-uniform, variable, tubular and/or tapered. In some embodiments, slot 120 has one or more of various surface configurations, for example, rough, threaded, arcuate, undulating, porous, semi-porous, dimpled, polished and/or textured.

Figure 6:
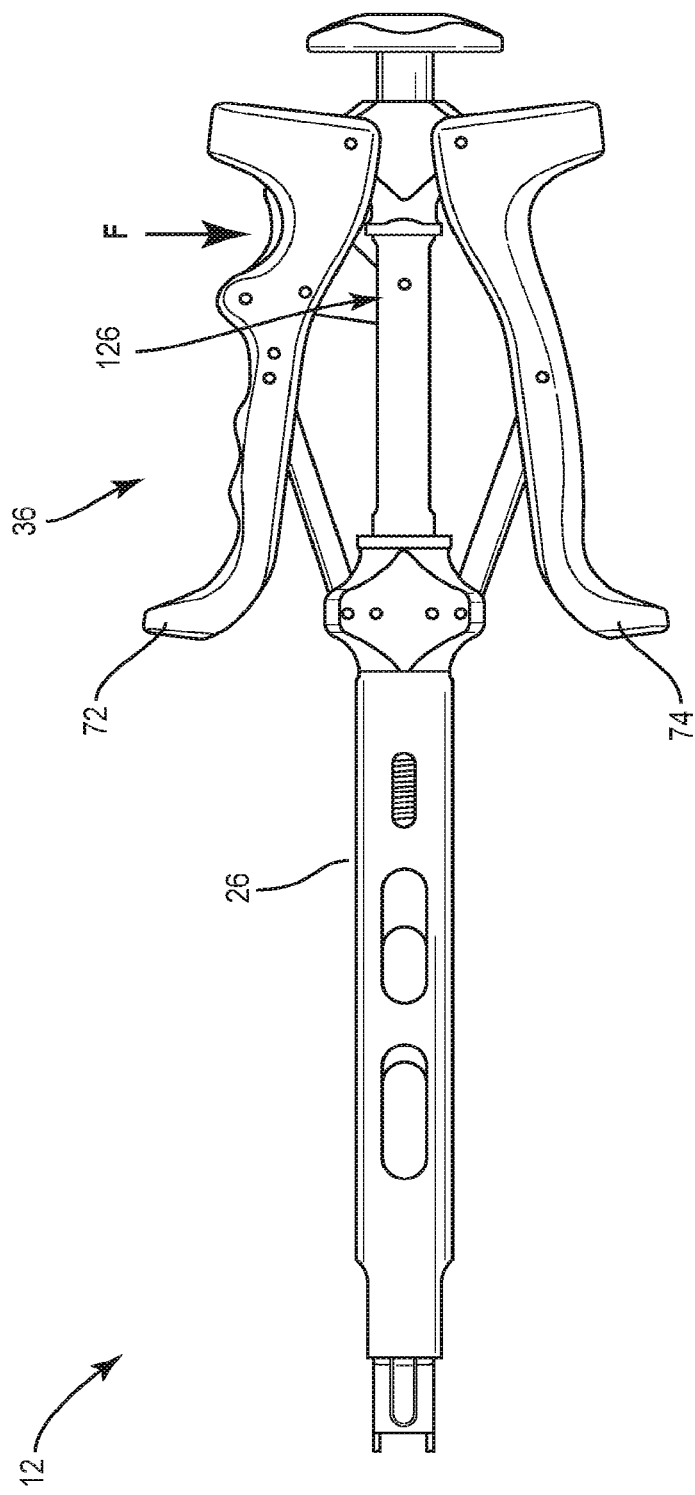
FIG. 6 is a side view of the components shown in FIG. 1.

Shaft 38 includes a surface that defines an opening 126, as shown in FIG. 6 that is configured for movable disposal of latch 40 such that latch 40 can translate through shaft 38 to engage pin 122. In some embodiments, opening 126 may have various cross-section configurations, for example, oval, oblong, triangular, rectangular, square, polygonal, irregular, uniform, non-uniform, variable, tubular and/or tapered.

Figure 9:
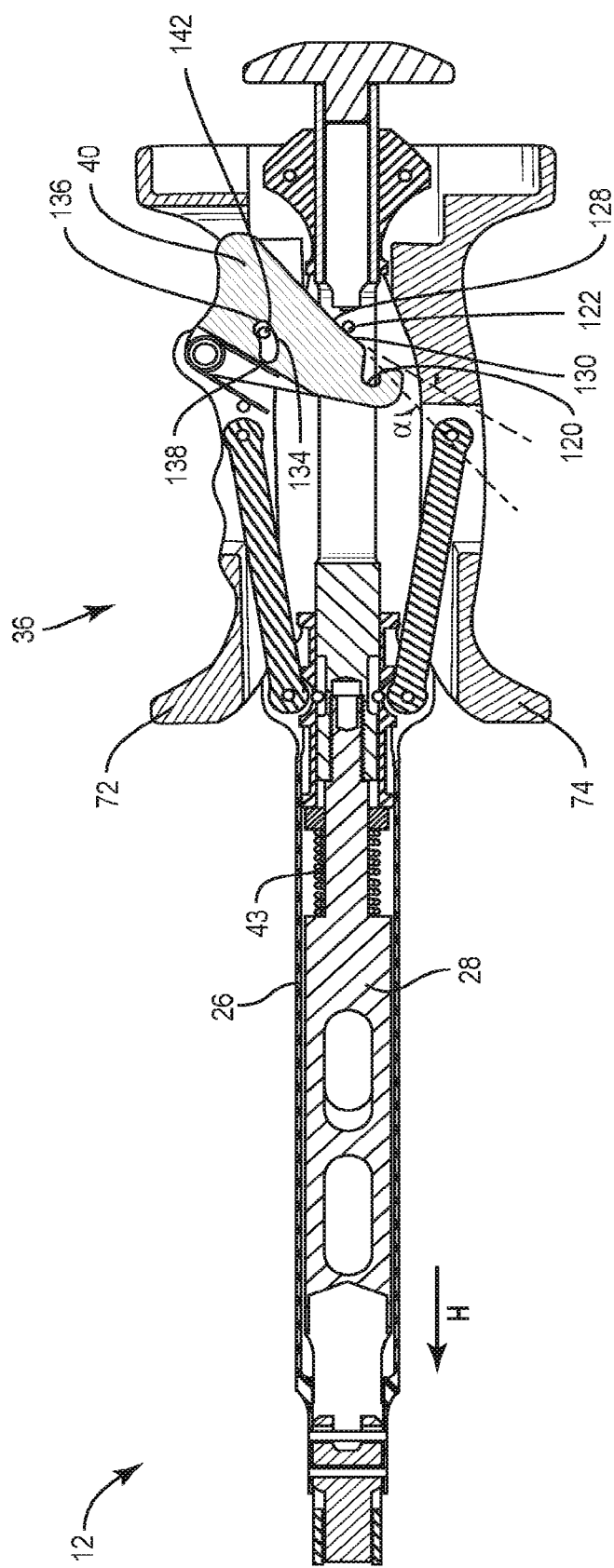
FIG. 9 is a side cross section view of the components shown in FIG. 8.

Latch 40 defines a ramp 128 and a ramp 130 disposed at a selected angular orientation a relative to ramp 128, as shown in FIGS. 3, 5, 7 and 9. Ramps 128, 130 are configured for slidable engagement with pin 122 to facilitate movement of actuator 36 relative to member 24 between the positions, as described herein. Slidable engagement between ramps 128, 130 and pin 122 is actuated via spring 113. In some embodiments, ramps 128, 130 enable actuator 36 to fully return to the open position from the closed position without actuator 36 becoming disposed in the intermediate position. Spring 43 provides the energy to return actuator 36 to the open position. In some embodiments, ramps 128, 130 are configured to enable inserter 12 to automatically return to the open position from the closed position. In some embodiments, ramps 128, 130 are configured to prevent inserter 12 from capture in the intermediate position via engagement between pin 122 and slot 120, as described herein. Ramps 128, 130 are relatively oriented to form angle a, as shown in FIG. 9. In some embodiments, angle α is in a range from greater than 0 to 90 degrees.

In the open position, as shown by arrows J in FIG. 2, latch 40 is oriented with actuator 36 in the non-locked orientation where pin 122 engages an end surface 132 of latch 40, as shown in FIG. 3. In the intermediate position, as shown by arrows C in FIG. 4, actuator 36 is manually compressed and pin 122 translates into slot 120 and engages a surface of slot 120 to orient latch 40 into the locked orientation, as shown in FIG. 5. Latch 40 is depressed, as shown by arrow F in FIG. 6, and spring 113 is biased and pin 122 engages ramp 130, as shown in FIG. 7. In the closed position, as shown by arrows G in FIG. 8, actuator 36 is manually compressed and pin 122 translates from ramp 130 to ramp 128 such that latch 40 is oriented into the non-locked orientation, as shown in FIG. 9.

Ramps 128, 130 enable inserter 12 to automatically return to an open position from the closed position and prevents inserter 12 from capture in the intermediate position. When actuator 36 is further compressed and released, inserter 12 automatically returns to the open position from the closed position. In some embodiments, actuator 36 is further compressed from the closed position and rapidly released to automatically return to the open position. In some embodiments, actuator 36 is further compressed from the closed position and slowly released such that actuator 36 returns to the intermediate position and latch 40 is depressible to return actuator 36 to the open position.

Figure 8:
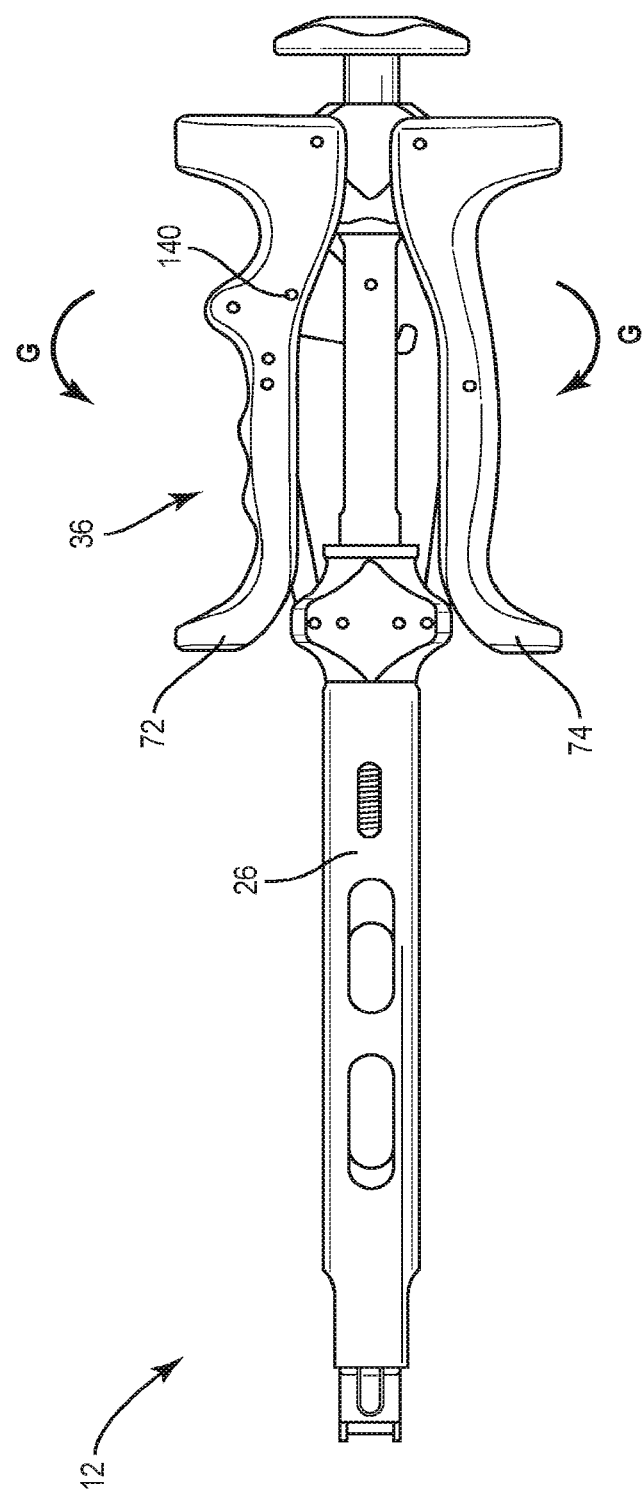
FIG. 8 is a side view of the components shown in FIG. 1.

Latch 40 includes a slot 134, as shown in FIG. 9. Slot 134 includes an end, for example, a rotatable limit 136 and an end, for example a rotatable limit 138. Limits 136, 138 are configured to limit the rotation of latch 40 relative to actuator 36. Handle 72 includes an opening 140, as shown in FIG. 8. A pin 142 is configured for disposal within slot 134 and opening 140 such that when latch 40 rotates, pin 142 abuts limits 136, 138. When actuator 36 is in the open position and latch 40 is in the non-locked orientation, pin 142 abuts with limit 138. In the intermediate position, latch 40 is disposed in the locked orientation such that pin 142 abuts limit 138. In the non-locked orientation, latch 40 is depressed via trigger 118 and pin 142 is disposed within an intermediate section 137, as shown in FIG. 7. In the closed position, latch 40 is disposed in the non-locked orientation, and pin 142 abuts limit 136, as shown in FIG. 9.

In operation, handles 72, 74 are movable to the open position, as shown by arrows J in FIG. 2, and latch 40 is disposed with actuator 36 in the non-locked orientation, as shown in FIG. 3. Receiver 14 is loaded into end 22 of inserter 12. In the open position, tabs 54, 56 are in a flexed outward direction, as shown by arrows B in FIG. 10, and tabs 54, 56 do not engage with openings 62, 64 of receiver 14.

Handles 72, 74 of actuator 36 are movable to the intermediate position, as shown by arrows C in FIG. 4, and latch 40 is disposed in the locked orientation, as shown in FIG. 5. Latch 40 locks with pin 122 via slot 120 to prevent handles 72, 74 from opening or closing. In the intermediate position, receiver 14 is connected to end 22 of inserter 12, as shown in FIG. 11. Sleeve 26 translates in a direction, for example, axially, as shown by arrow E in FIG. 11 and sleeve 28 remains fixed relative to sleeve 26 when handles 72, 74 are compressed, for example, in an inward direction, shown by arrows C in FIG. 4. End 66 of tip 30 translates axially and tabs 54, 56 are compressed by the sleeve 26 to engage openings 62, 64 of receiver 14.

Trigger 118 is depressed, as shown by arrow F in FIG. 6 and handles 72, 74 are compressed, for example, in an inward direction as shown by arrows G in FIG. 8, such that sleeve 26 translates axially, as shown by arrow H in FIG. 9. Handles 72, 74 are movable to the closed position, as shown by arrows G in FIG. 8, and latch 40 is disposable in the non-locked orientation, as shown in FIG. 9. In the closed position, end 66 of tip 30 translates axially, as shown by arrow I in FIG. 12 and receiver 14 remains connected to end 22 of inserter 12 via tabs 54, 56 as sleeve 26 continues to translate over tabs 54, 56. End 66 of tip 30 drives crown 68 axially, as shown by arrow I in FIG. 12. Handles 72, 74 are further compressed from the closed position and rapidly released to automatically return to the open position, and receiver 14 is released from end 22.

In assembly, operation and use, surgical system 10, is employed with a surgical procedure, for example, a surgical treatment of an applicable condition or injury of an affected section of a spinal column and adjacent areas within a body. In some embodiments, surgical system 10 can be used in any surgical method or technique including open surgery, mini-open surgery, minimally invasive surgery and percutaneous surgical implantation, whereby vertebrae V is accessed, such as through a mini-incision, and possibly also via a sleeve (not shown) that provides a protected passageway to vertebrae V. Once access to the surgical site is obtained, the particular surgical procedure can be performed for treating the spine disorder.

An incision is made in the body of a patient and a cutting instrument (not shown) creates a surgical pathway. A preparation instrument (not shown) can be employed to prepare tissue surfaces of or surrounding vertebrae V, as well as for aspiration and irrigation of a surgical region. Pilot hole(s) (not shown) are made with the selected areas of bone, for example vertebrae V for receiving shaft 18, as shown in FIG. 15.

Handles 72, 74, as described herein, are movable to the open position, as shown by arrows J in FIG. 2, and latch 40 is disposed with actuator 36 in the non-locked orientation, as shown in FIG. 3. Receiver 14 is loaded to end 22 of inserter 12, as described herein, in a direction shown by arrow A in FIG. 10. Handles 72, 74 of actuator 36 are movable to the intermediate position, as shown by arrows C in FIG. 4, and latch 40 is disposed in the locked orientation, as shown in FIG. 5. In the intermediate position, receiver 14 is connected to end 22 of inserter 12, as shown in FIG. 11. Sleeve 26 translates axially, as shown by arrow D in FIG. 5 and end 66 of tip 30 translates axially, shown by arrow E in FIG. 11 such that tabs 54, 56 are compressed by the sleeve 26 to engage openings 62, 64 of receiver 14.

Handles 72, 74 are movable to the closed position, as shown by arrows G in FIG. 8, and latch 40 is disposable in the non-locked orientation, as shown in FIG. 9. Trigger 118 is depressed, as shown by arrow F in FIG. 6 and handles 72, 74 are compressed in an inward direction as shown by arrows G in FIG. 8, such that sleeve 26 translates axially, as shown by arrow H in FIG. 9. In the closed position, end 66 of tip 30 translates axially, as shown by arrow I in FIG. 12 and receiver 14 is connected to end 22 of inserter 12 via tabs 54, 56 as sleeve 26 continues to translate over tabs 54, 56. End 66 of tip 30 drives crown 68 axially, as shown by arrow I in FIG. 12. Handles 72, 74 are further compressed from the closed position and rapidly released to automatically return to the open position, and receiver 14 is released from end 22.

Upon completion of a procedure, inserter 12, additional surgical instruments and/or tools, assemblies and non-implanted components of surgical system 10 are removed and the incision(s) are closed. One or more of the components of surgical system 10 can be made of radiolucent materials such as polymers. Radiomarkers may be included for identification under x-ray, fluoroscopy, CT or other imaging techniques. In some embodiments, the use of surgical navigation, microsurgical and image guided technologies may be employed to access, view and repair spinal deterioration or damage, with the aid of surgical system 10.

In some embodiments, surgical system 10 may include one or a plurality of plates, connectors and/or bone fasteners for use with a single vertebral level or a plurality of vertebral levels. In some embodiments, one or more of bone fasteners may be engaged with tissue in various orientations, for example, series, parallel, offset, staggered and/or alternate vertebral levels. In some embodiments, one or more bone fasteners may comprise multi-axial screws, sagittal angulation screws, pedicle screws, mono-axial screws, uni-planar screws, facet screws, fixed screws, tissue penetrating screws, conventional screws, expanding screws, wedges, anchors, buttons, clips, snaps, friction fittings, compressive fittings, expanding rivets, staples, nails, adhesives, posts, fixation plates and/or posts.

In some embodiments, surgical system 10 includes an agent, which may be disposed, packed, coated or layered within, on or about the components and/or surfaces of surgical system 10. In some embodiments, the agent may include bone growth promoting material, for example, bone graft to enhance fixation of the fixation elements with vertebrae. In some embodiments, the agent may be HA coating. In some embodiments, the agent may include one or a plurality of therapeutic agents and/or pharmacological agents for release, including sustained release, to treat, for example, pain, inflammation and degeneration.

Figure 17:
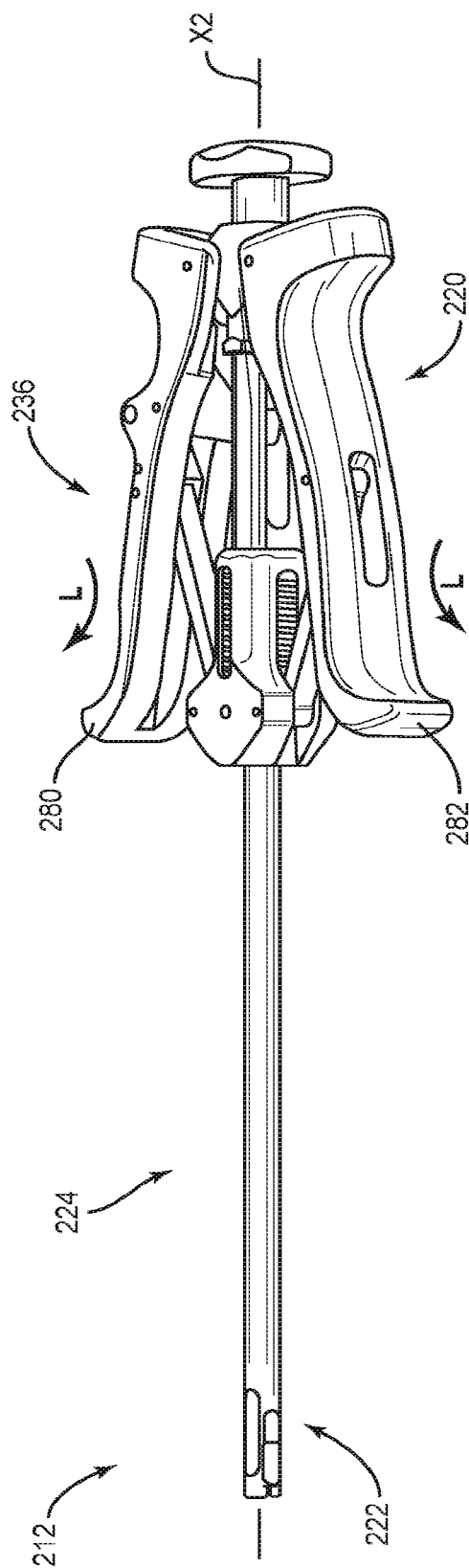
FIG. 17 is a perspective view of the components shown in FIG. 16.
Figure 22:
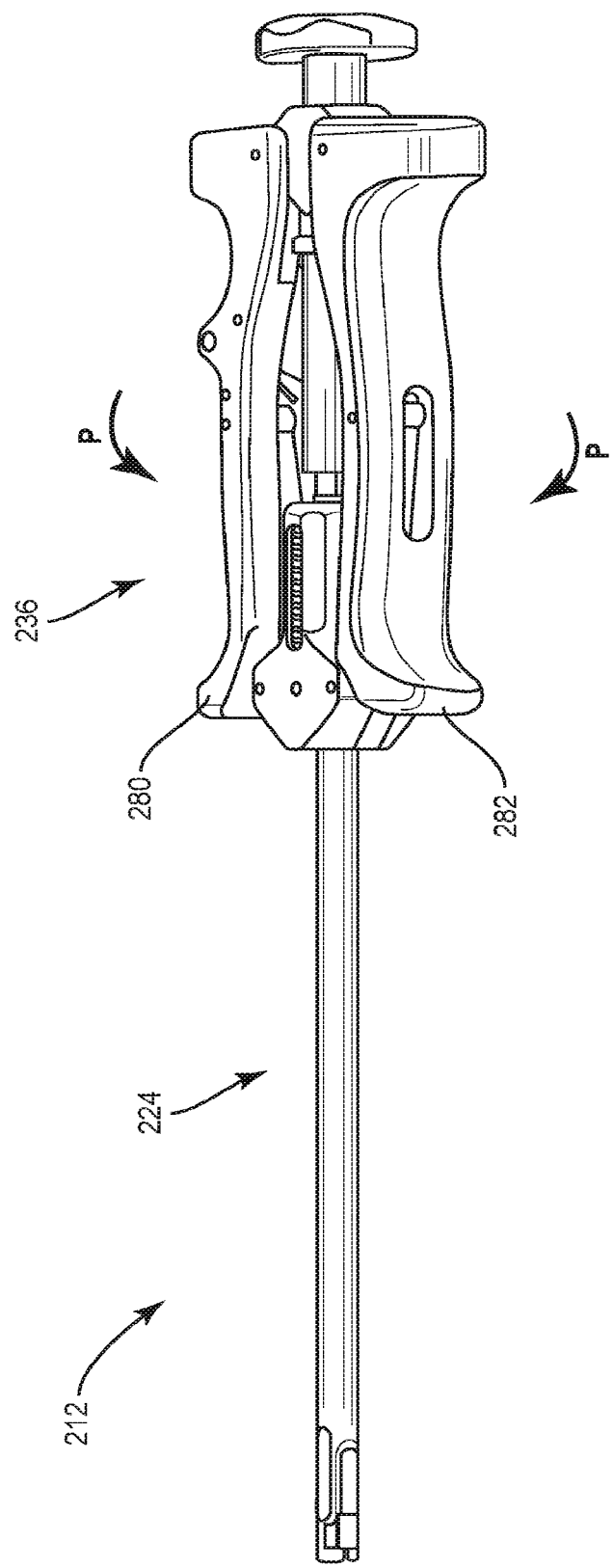
FIG. 22 is a perspective view of the components shown in FIG. 16.
Figure 23:
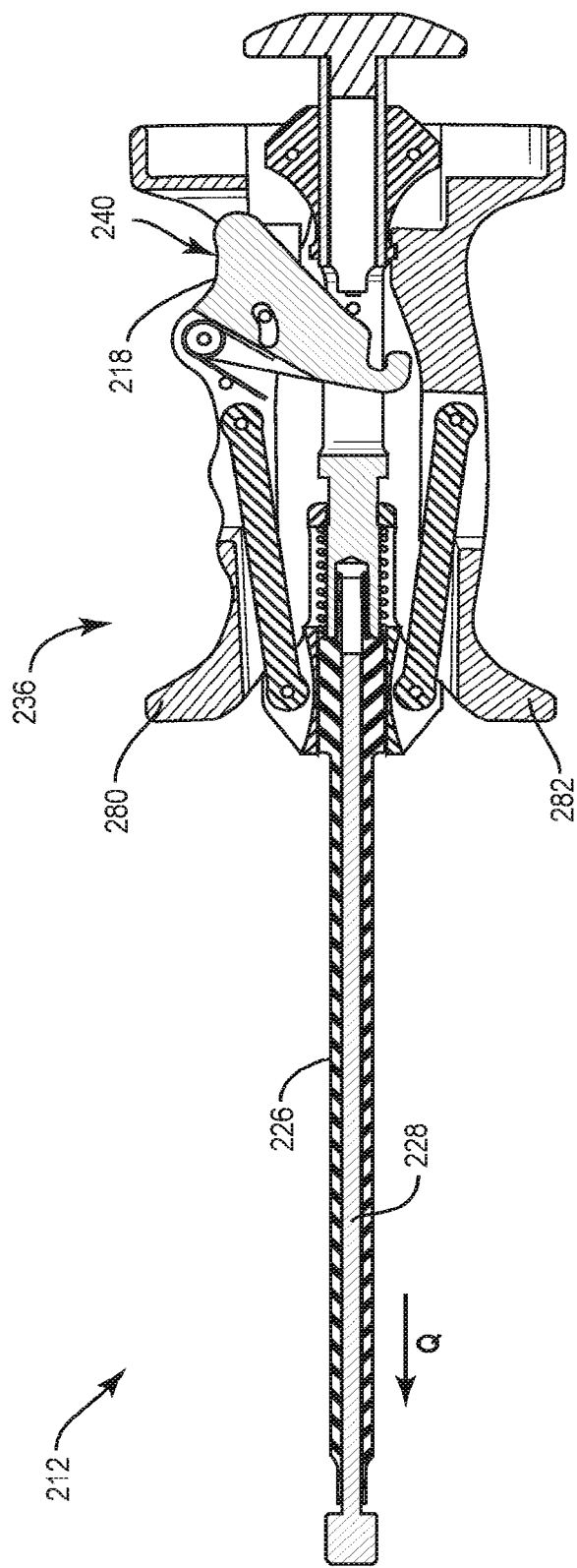
FIG. 23 is a side cross section view of the components shown in FIG. 22.
Figure 24:
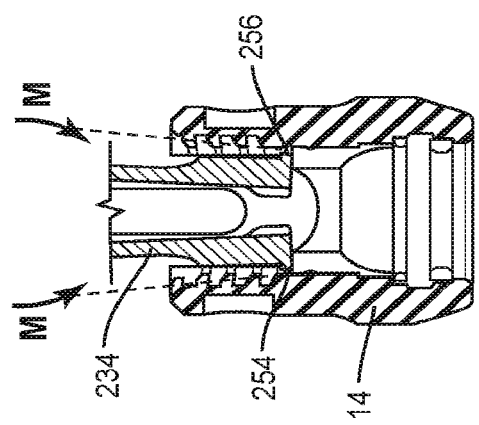
FIG. 24 is a side cross section view of components of one embodiment of a surgical system in accordance with the principles of the present disclosure.

In one embodiment, as shown in FIGS. 16-26, surgical system 10, includes an inserter 212, similar to inserter 12 described herein, configured for use with receiver 14, as shown in FIG. 24. See also, for example, the embodiments and disclosure of an inserter and method for surgically treating a spine, shown and described in commonly owned and assigned U.S. patent application Ser. No. 17/078,648 filed Oct. 23, 2020, and published as U.S. Patent Application Publication No. US-2022-0125488-A1, on Apr. 28, 2022, the entire contents of which being incorporated herein by reference. Inserter 212 includes a proximal end 220 and a distal end 222, as shown in FIG. 17. Inserter 212 extends along and defines a longitudinal axis X2, as shown in FIG. 17.

Figure 18:
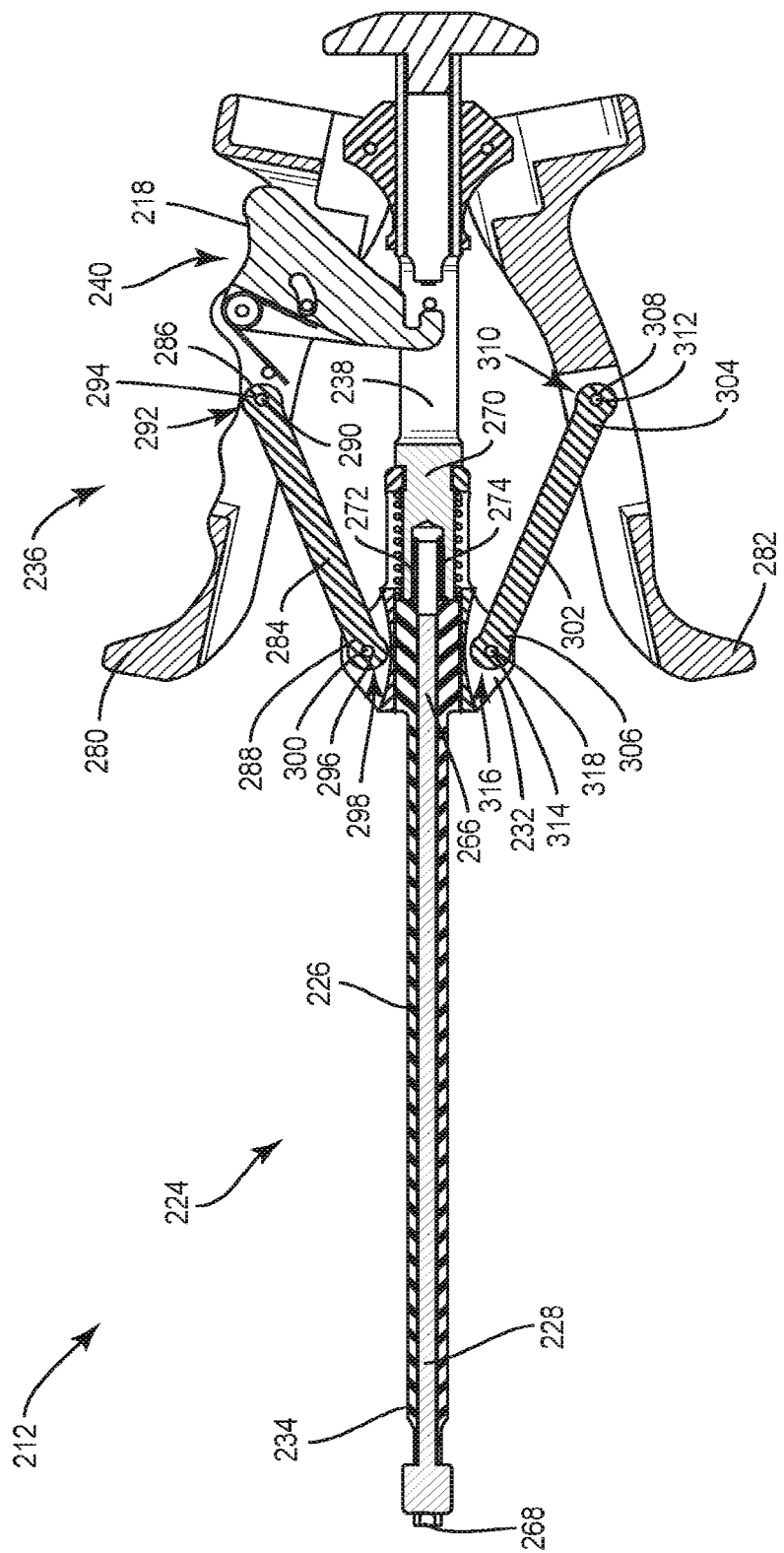
FIG. 18 is a side cross section view of the components shown in FIG. 17.

Inserter 212 includes a member 224, including an outer sleeve 226 and an inner shaft 228, as shown in FIG. 18. Sleeve 226 and shaft 228 are configured to engage receiver 14. Sleeve 226 includes an end 232 and an end 234, as shown in FIG. 18. In some embodiments, sleeve 226 may have various cross-section configurations, for example, oval, oblong, triangular, rectangular, square, polygonal, irregular, uniform, non-uniform, variable, tubular and/or tapered.

End 232 is configured to engage an actuator 236, similar to actuator 36, as shown in FIG. 18. Actuator 236 is movable relative to member 224, as described herein. An outer shaft 238 is disposed at end 232 and is configured to engage actuator 236 and a latch 240, similar to latch 40 described herein, as shown in FIG. 18. In some embodiments, shaft 238 may have various cross-section configurations, for example, oval, oblong, triangular, rectangular, square, polygonal, irregular, uniform, non-uniform, variable, tubular and/or tapered.

Figure 26:
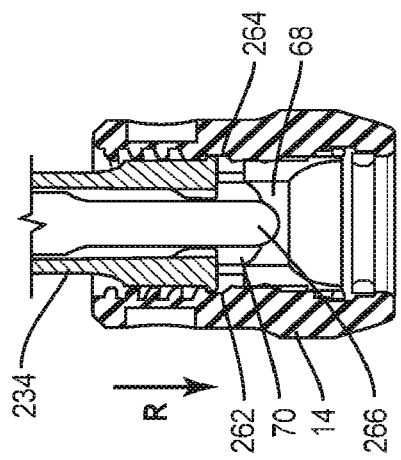
FIG. 26 is a side cross section view of the components shown in FIG. 24.
Figure 25:
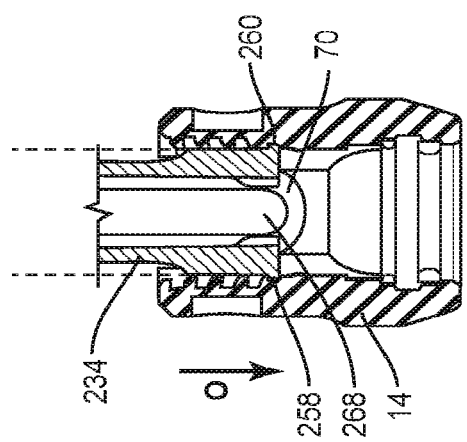
FIG. 25 is a side cross section view of the components shown in FIG. 24.

End 234 is configured to engage an inner surface of receiver 14, as shown in FIGS. 24-26. End 234 includes a tab 254 and a tab 256. Tabs 254 and 256 are flexible and are configured to engage receiver 14. Tab 254 includes an outer surface that defines a projection 258 and tab 256 includes an outer surface that defines a projection 260, as shown in FIG. 25. Projections 258, 260 are configured to engage grooves 262, 264 defined from an inner surface of receiver 14, as shown in FIG. 26.

Shaft 228 includes an end 266 and an end 268, as shown in FIG. 18. Shaft 228 is in coaxial alignment relative to sleeve 226 and extends along longitudinal axis X2. Shaft 228 is movable relative to sleeve 226. In some embodiments, shaft 228 may have various cross-section configurations, for example, oval, oblong, triangular, rectangular, square, polygonal, irregular, uniform, non-uniform, variable, tubular and/or tapered.

End 266 is configured to engage an end 270 of shaft 238, as shown in FIG. 18. End 266 includes a threaded portion 272 that is configured for disposal into a threaded recess 274 of end 270, as shown in FIG. 18. Shaft 228 is fixed to shaft 238 and shaft 228 is movable relative to sleeve 226, as shown in FIGS. 18, 20, 21 and 23. A biasing member, for example, a spring 278 is configured for disposal about end 270 and is configured to provide energy in an axial direction to facilitate return movement of shaft 228 when actuator 236 is released, as described herein.

End 268 is configured to engage crown 68 disposed within cavity 70 of receiver 14, as shown in FIG. 26. Crown 68 is configured for locking receiver 14 to shaft 18, as described herein. In some embodiments, end 268 may have various cross-section configurations, for example, oval, oblong, triangular, rectangular, square, polygonal, irregular, uniform, non-uniform, variable, tubular and/or tapered.

End 220 of inserter 212 includes actuator 236, as shown in FIG. 17. Actuator 236 is movable between an open position including a non-locked orientation (FIGS. 17 and 18), an intermediate position including a locked orientation (FIGS. 19 and 20) and a closed position including a non-locked orientation (FIGS. 22 and 23), as described herein. Actuator 236 is rotatable relative to sleeve 226 such that shaft 228 translates relative to sleeve 226 to engage receiver 14. In a natural state, actuator 236 is biased to the open position and is automatically movable from the closed position to the open position. Actuator 236 includes a pair of lever handles 280, 282, as shown in FIG. 17 that are rotatable relative to member 224.

Figure 20:
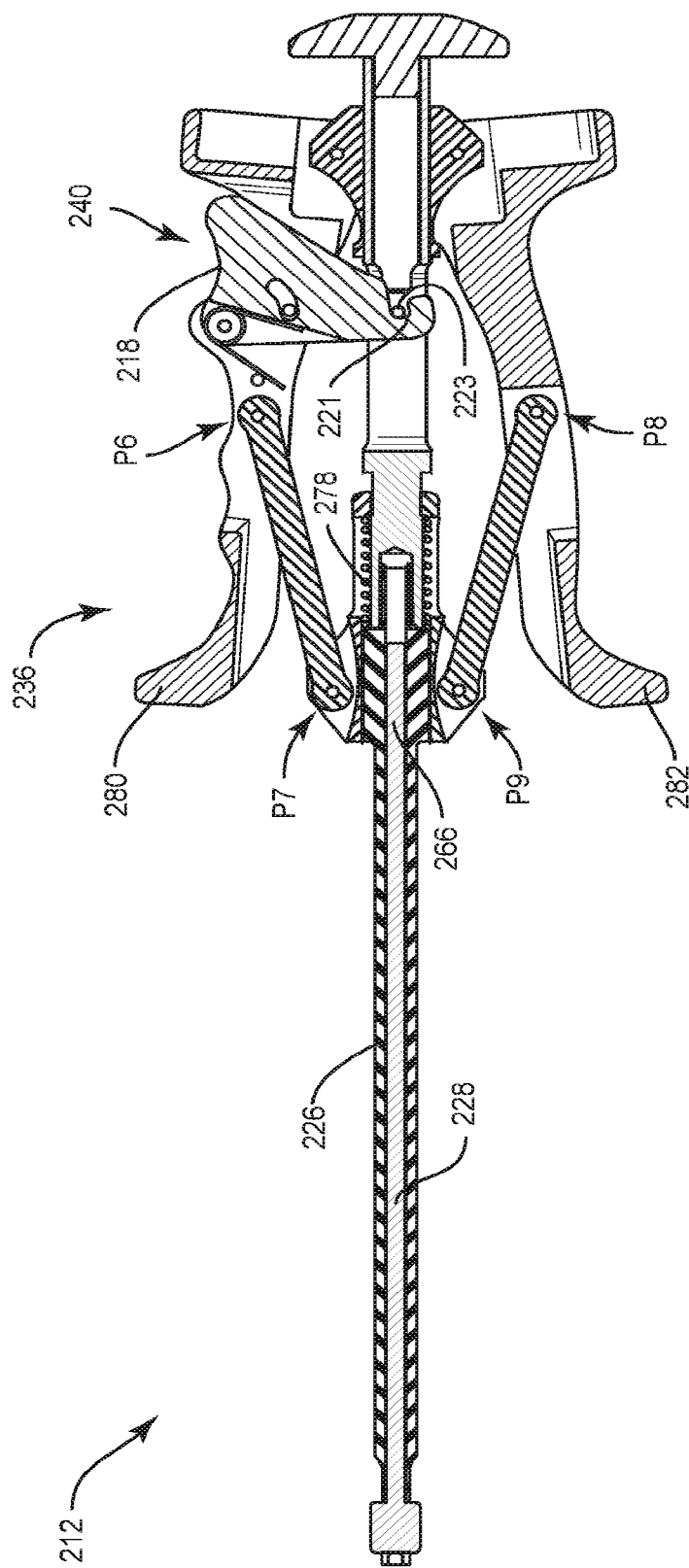
FIG. 20 is a side cross section view of the components shown in FIG. 19.
Figure 21:
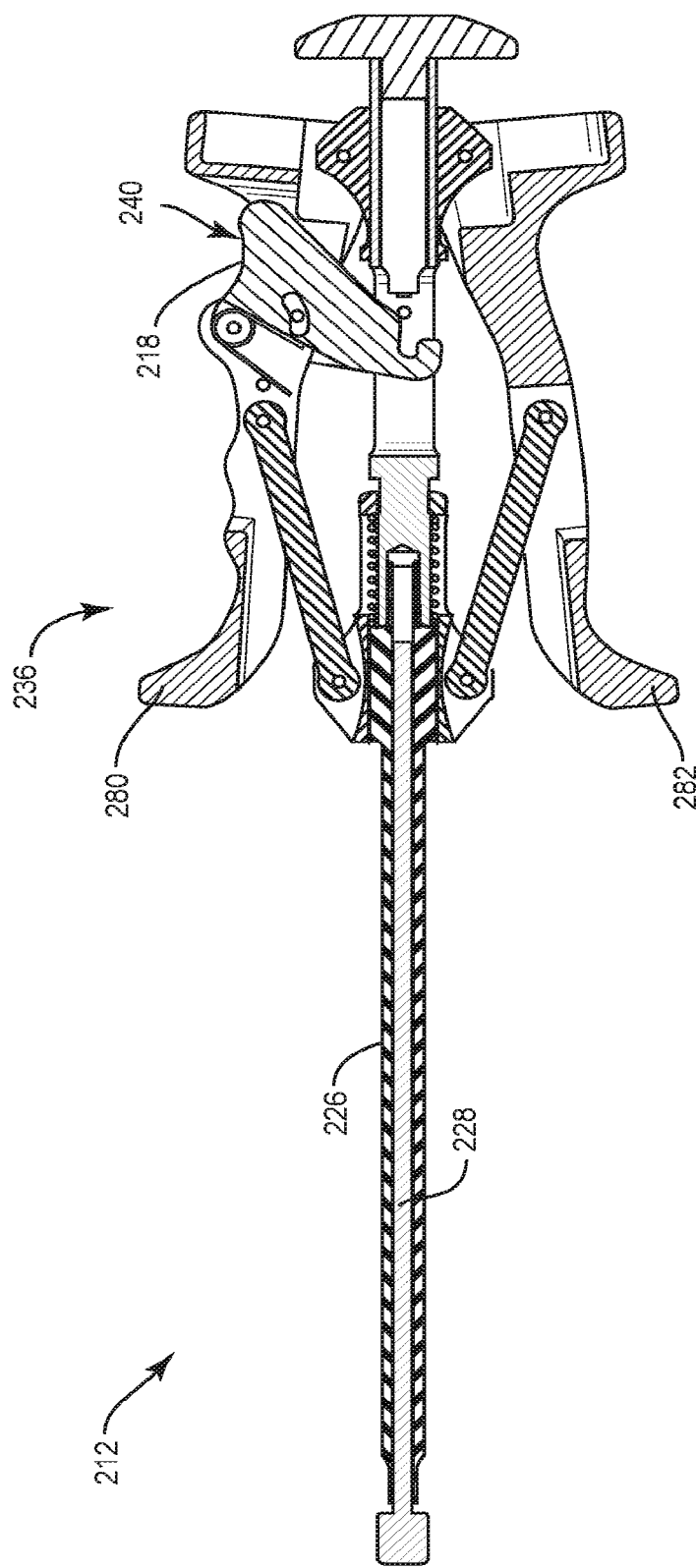
FIG. 21 is a side cross section view of the components shown in FIG. 19.

Handle 280 includes a bar linkage 284 that is rotatably engaged to member 224, as shown in FIG. 18. Linkage 284 includes an end 286 and an end 288. End 286 includes a surface that defines an opening 290. A surface of handle 280 defines an opening 292. End 286 engages handle 280 via a pin 294 that is disposed within openings 290 and 292. End 288 includes a surface that defines an opening 296. A surface of sleeve 226 defines an opening 298. End 288 engages sleeve 226 via a pin 300 that is disposed within openings 296 and 298. Engagement between end 286 of linkage 284 and handle 280 creates a pivot point P6, as shown in FIG. 20. Engagement between end 288 of linkage 284 and sleeve 226 creates a pivot point P7, as shown in FIG. 20.

Handle 282 includes a bar linkage 302 rotatably engaged to member 224, as shown in FIG. 18. Linkage 302 includes an end 304 and an end 306. End 304 includes a surface that defines an opening 308. A surface of handle 282 defines an opening 310. End 304 engages handle 282 via a pin 312 that is disposed within openings 308 and 310. End 306 includes a surface that defines an opening 314. A surface of sleeve 226 defines an opening 316. End 306 engages sleeve 226 via a pin 318 that is disposed within openings 314 and 316. Engagement between end 304 of linkage 302 and handle 282 creates a pivot point P8, as shown in FIG. 20. Engagement between end 306 of linkage 302 and sleeve 226 creates a pivot point P9, as shown in FIG. 20.

Latch 240 is connected to actuator 236 in a non-locked orientation (FIGS. 17-18 and 22-22) such that actuator 236 is movable relative to member 224 in the open position and closed position, and a locked orientation (FIGS. 19 and 20) such that actuator 236 is fixed relative to member 224 in the intermediate position. Latch 240 is connected to actuator 236 via handle 280, in the same manner as latch 40 is connected to actuator 36, described above with regard to FIGS. 1-15.

In operation, handles 280, 282 are movable to the open position, as shown by arrows L in FIG. 17, and latch 240 is disposed to actuator 236 in the non-locked orientation, as shown in FIG. 18. Receiver 14 is loaded into end 222 of inserter 212. In the open position, tabs 254, 256 are in a flexed inward direction, as shown by arrows M in FIG. 24, and tabs 254, 256 do not engage grooves 262, 264 of receiver 14.

Figure 19:
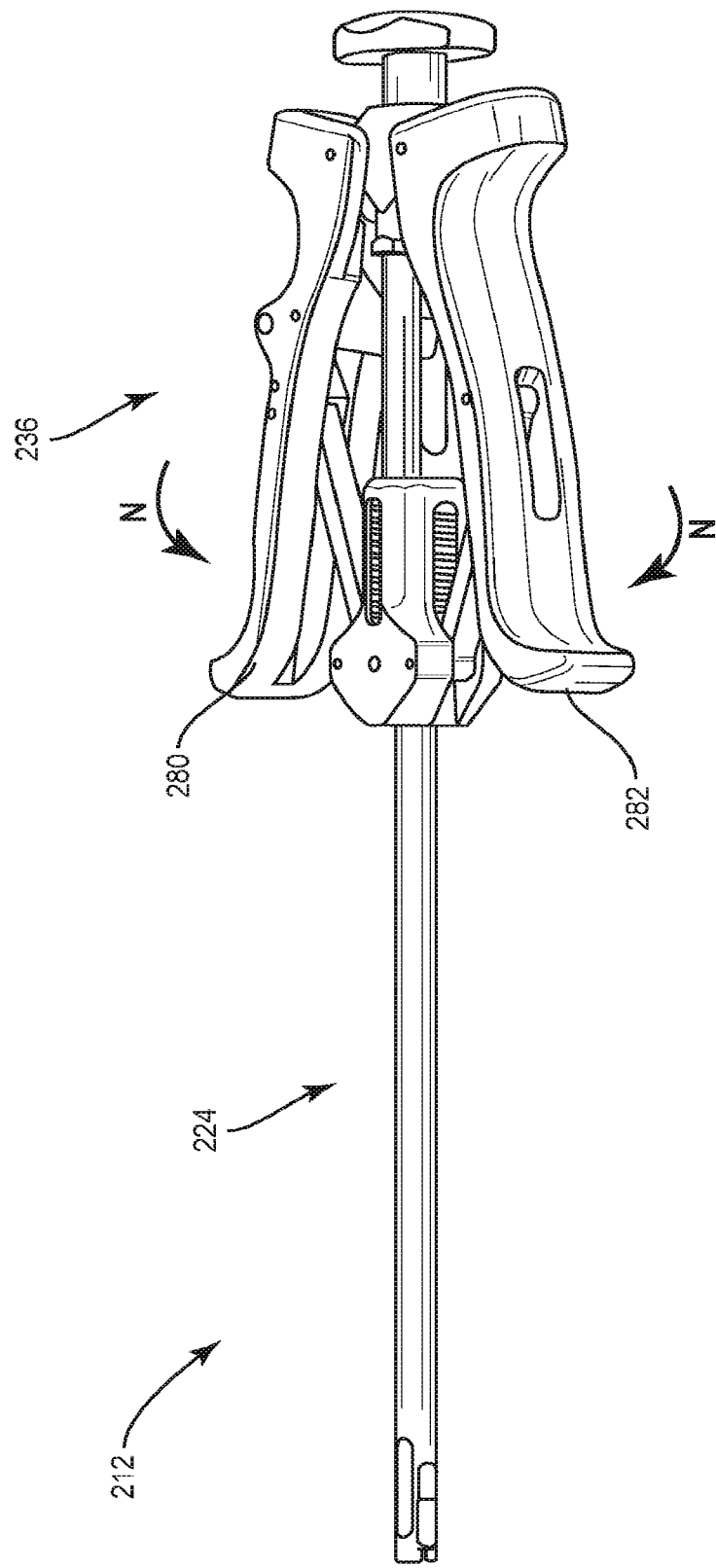
FIG. 19 is a perspective view of the components shown in FIG. 16.

Handles 280, 282 of actuator 236 are movable to the intermediate position, as shown by arrows N in FIG. 19, and latch 240 is disposed in the locked orientation, as shown in FIG. 20. Latch 240 locks with a pin 223, similar to pin 122 via a slot 221, similar to slot 120 to prevent handles 280, 282 from opening or closing. In the intermediate position, receiver 14 is connected to end 222 of inserter 212, as shown in FIG. 25. Shaft 228 translates in a direction, for example, axially, as shown by arrow O in FIG. 25 and sleeve 226 remains fixed relative to shaft 228 when handles 280, 282 are compressed, for example, in an inward direction, shown by arrows N. End 268 of shaft 228 translates axially and tabs 254, 256 are compressed by an interior surface of receiver 14 to engage grooves 262, 264 of receiver 14.

Handles 280, 282 are movable to the closed position, as shown by arrows P in FIG. 22, and latch 240 is disposable in the non-locked orientation, as shown in FIG. 23. Trigger 218, similar to trigger 118 is depressed and handles 280, 282 are compressed, for example, in an inward direction, as shown by arrows P in FIG. 22 such that shaft 228 translates axially, as shown by arrow Q in FIG. 23 and sleeve 226 remains fixed relative to shaft 228. In the closed position, end 268 of shaft 228 translates axially, as shown by arrow R in FIG. 26 and receiver 14 is connected to end 222 of inserter 212 via tabs 254, 256 as shaft 228 continues to translate through tabs 254, 256. End 268 of shaft 228 drives crown 68 axially, as shown by arrow R in FIG. 26. Handles 280, 282 are further compressed from the closed position and rapidly released to automatically return to the open position, and receiver 14 is released from end 222.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A surgical instrument comprising:
an outer sleeve;
spaced apart tabs extending from a distal end of the outer sleeve such that the tabs are flexible relative to the outer sleeve;
an intermediate sleeve positioned within the outer sleeve;
a shaft coupled to the intermediate sleeve, the intermediate sleeve comprising a threaded portion disposed in a threaded recess of the shaft; and
an actuator comprising opposite lever handles each having a first end that is coupled to the shaft and a second end that is coupled to the outer sleeve via a linkage such that simultaneous rotation of the lever handles relative to the shaft and the sleeves translates the intermediate sleeve relative to the outer sleeve.

2. The surgical instrument recited in claim 1, wherein the tabs are monolithically formed with the outer sleeve.

3. The surgical instrument recited in claim 1, further comprising a latch connected to the actuator and configured to move the surgical instrument between a non-locked orientation wherein the lever handles are movable relative to the shaft and the sleeves and a locked orientation wherein the lever handles are fixed relative to the shaft and the sleeves.

4. The surgical instrument recited in claim 3, wherein the latch extends through one of the lever handles.

5. The surgical instrument recited in claim 3, wherein the shaft includes a pin extending from an outer surface of the shaft, the latch comprising a slot, the pin being spaced apart from the slot when the surgical instrument is in the non-locked orientation.

6. The surgical instrument recited in claim 3, wherein the shaft includes a pin extending from an outer surface of the shaft, the latch comprising a slot, the pin being positioned in the slot when the surgical instrument is in the locked orientation.

7. The surgical instrument recited in claim 3, further comprising a torsion spring coupled to one of the lever handles and the latch to provide torque to the latch.

8. The surgical instrument recited in claim 1, wherein rotation of the lever handles relative to the shaft and the sleeves translates the intermediate sleeve relative to the outer sleeve between an open position wherein a distal tip of the intermediate sleeve is positioned proximal to distal end surfaces of the tabs and a closed position wherein the distal tip extends distal to the distal end surfaces of the tabs.

9. The surgical instrument recited in claim 8, wherein the surgical instrument moves from the open position to the closed position by moving the second ends toward one another.

10. The surgical instrument recited in claim 8, wherein the surgical instrument is biased to the open position.

11. The surgical instrument recited in claim 8, wherein the surgical instrument is biased to the open position by a spring.

12. The surgical instrument recited in claim 8, wherein the surgical instrument is biased to the open position by a spring, the spring being disposed about the shaft, the spring having a first end that engages the intermediate sleeve and an opposite second end that engages the shaft.

13. The surgical instrument recited in claim 1, wherein the tabs each include a projection extending from an outer surface thereof.

14. The surgical instrument recited in claim 13, wherein the projections face away from one another.

15. A surgical system comprising:
a bone fastener comprising a head having spaced apart arms defining an implant cavity therebetween, the arms each including a groove; and
a surgical instrument comprising:
- an outer sleeve,
- spaced apart tabs extending from a distal end of the outer sleeve such that the tabs are flexible relative to the outer sleeve, the tabs being positioned in the implant cavity,
- an intermediate sleeve positioned within the outer sleeve,
- a shaft coupled to the intermediate sleeve, the intermediate sleeve comprising a threaded portion disposed in a threaded recess of the shaft, and
- an actuator comprising opposite lever handles each having a first end that is coupled to the shaft and a second end that is coupled to the outer sleeve via a linkage,
wherein simultaneous rotation of the lever handles relative to the shaft and the sleeves translates the intermediate sleeve relative to the outer sleeve to move the surgical instrument from a first orientation in which the tabs are spaced apart from the grooves and a second orientation in which the tabs are each disposed in one of the grooves.

16. The surgical system recited in claim 15, wherein a distal tip of the intermediate sleeve is positioned proximal to distal end surfaces of the tabs when the surgical instrument is in the first orientation and the distal tip extends distal to the distal end surfaces of the tabs when the surgical instrument is in the second orientation.

17. The surgical system recited in claim 15, wherein the surgical instrument is biased to the first orientation by a spring.

18. The surgical system recited in claim 15, wherein the surgical instrument is biased to the first orientation by a spring, the spring being disposed about the shaft, the spring having a first end that engages the intermediate sleeve and an opposite second end that engages the shaft.

19. The surgical system recited in claim 15, further comprising a latch connected to the actuator and configured to move the surgical instrument between a non-locked orientation wherein the lever handles are movable relative to the shaft and the sleeves and a locked orientation wherein the lever handles are fixed relative to the shaft and the sleeves.

20. A surgical system comprising:
a bone fastener comprising a head having spaced apart arms defining an implant cavity therebetween, the arms each including a groove; and
a surgical instrument comprising:
an outer sleeve,
spaced apart tabs extending from a distal end of the outer sleeve such that the tabs are flexible relative to the outer sleeve, the tabs being positioned in the implant cavity,
an intermediate sleeve positioned within the outer sleeve,
a shaft coupled to the intermediate sleeve,
an actuator comprising opposite lever handles each having a first end that is coupled to the shaft and a second end that is coupled to the outer sleeve via a linkage, and
a latch connected to the actuator and configured to move the surgical instrument between a non-locked orientation wherein the lever handles are movable relative to the shaft and the sleeves and a locked orientation wherein the lever handles are fixed relative to the shaft and the sleeves, the latch extending through one of the lever handles,
wherein simultaneous rotation of the lever handles relative to the shaft and the sleeves translates the intermediate sleeve relative to the outer sleeve to move the surgical instrument from a first orientation in which the tabs are spaced apart from the grooves and a second orientation in which the tabs are each disposed in one of the grooves.

* * * * *